(12) United States Patent
Bulleit et al.

(10) Patent No.: US 11,931,281 B1
(45) Date of Patent: Mar. 19, 2024

(54) ADJUSTABLE BRACE AND PROCESSES FOR MAKING AND USING SAME

(71) Applicant: Protect3d, Inc., Durham, NC (US)

(72) Inventors: Clark Harrison Bulleit, Tampa, FL (US); Kevin Andrew Gehsmann, Greensboro, NC (US); Timothy John Skapek, Dallas, TX (US); Brian Rock, Raleigh, NC (US); Jaeah Yoo, Durham, NC (US)

(73) Assignee: PROTECT3D, INC., Durham, NC (US)

( * ) Notice: Subject to any disclaimer, the term of this patent is extended or adjusted under 35 U.S.C. 154(b) by 0 days.

(21) Appl. No.: 18/148,773

(22) Filed: Dec. 30, 2022

(51) Int. Cl.
  *A61F 5/01* (2006.01)
  *A61F 2/50* (2006.01)
  *B33Y 80/00* (2015.01)

(52) U.S. Cl.
  CPC .......... *A61F 5/0102* (2013.01); *A61F 2/5046* (2013.01); *B33Y 80/00* (2014.12); *A61F 2005/0167* (2013.01)

(58) Field of Classification Search
  CPC ................. A61F 5/0102; A61F 2/5046; A61F 2005/0167; A61F 5/05; B33Y 80/00
  See application file for complete search history.

(56) References Cited

U.S. PATENT DOCUMENTS

| | | | |
|---|---|---|---|
| 5,836,902 A | 11/1998 | Gray | |
| 10,231,862 B2 | 3/2019 | Summit | |
| 10,758,396 B2 * | 9/2020 | Rivlin | A61F 5/05866 |
| 10,932,940 B2 | 3/2021 | Karasahin | |
| 10,940,031 B2 | 3/2021 | Mark | |
| 2017/0079830 A1 | 3/2017 | Chhatrala | |

(Continued)

FOREIGN PATENT DOCUMENTS

| | | | | |
|---|---|---|---|---|
| CN | 105342741 A | * | 2/2016 | ............... A61F 5/05 |
| CN | 205041591 U | | 2/2016 | |

(Continued)

OTHER PUBLICATIONS

Anusci, Victor. "Activarmor May Have Finally Cracked the 3D Printed Cast/Orthosis Riddle." 3D Printing Media Network—The Pulse of the AM Industry, Mar. 19, 2018, https://www.3dprintingmedia.network/activarmor-may-finally-cracked-3d-printed-cast-orthosis-riddle/.

(Continued)

*Primary Examiner* — Tarla R Patel
(74) *Attorney, Agent, or Firm* — Husch Blackwell LLP; Bryan D. Stewart; Andrew C. Landsman

(57) ABSTRACT

An adjustable brace for stabilizing a body part of a patient and a method of fabricating such a brace is provided. In some embodiments, the adjustable brace comprises a first 3D printed stabilizer having a first exterior surface, a first interior surface, and a first thickness; a second stabilizer comprising a second exterior surface, a second interior surface, and a second thickness; one or more attachment points; and one or more selective engagement structures, wherein the first 3D printed stabilizer selectively engages with the second 3D printed stabilizer at common peripheries of the first 3D printed stabilizer and second 3D printed stabilizer via the one or more selective engagement structures, respectively; and a position of the first 3D printed stabilizer is adjustable in relation to the second 3D printed stabilizer.

8 Claims, 20 Drawing Sheets

(56) References Cited

U.S. PATENT DOCUMENTS

| | | | |
|---|---|---|---|
| 2019/0117432 A1* | 4/2019 | Park | A61F 5/028 |
| 2019/0240057 A1 | 8/2019 | Gunnsteinsson | |
| 2019/0269558 A1 | 9/2019 | Sheehan | |
| 2020/0069454 A1 | 3/2020 | Hall | |

FOREIGN PATENT DOCUMENTS

| | | | | |
|---|---|---|---|---|
| CN | 105434092 A | * | 3/2016 | |
| CN | 105853038 A | | 8/2016 | |
| CN | 205612603 U | | 10/2016 | |
| CN | 106361487 A | | 2/2017 | |
| CN | 107280841 A | | 10/2017 | |
| CN | 105963061 B | | 12/2017 | |
| CN | 108938171 A | * | 12/2018 | A61F 5/012 |
| CN | 110115652 A | * | 8/2019 | A61F 5/05 |
| CN | 114404123 A | * | 4/2022 | |
| EP | 3102162 B1 | * | 11/2021 | A61F 5/0127 |
| GB | 2580413 A1 | | 7/2020 | |
| WO | WO-2021156894 A1 | * | 8/2021 | A61F 5/05808 |

OTHER PUBLICATIONS

Airwolf 3D. "Amphibianskin Offers an Affordable 3D Printed Splint to Help the Healing Process." Airwolf 3D, Jan. 28, 2019, https://airwolf3d.com/2014/10/21/3d-printed-splint/.

Knowles, Kitty. "Castprint Is 3D Printing Beautiful Healthtech." Sifted, Aug. 4, 2019, https://sifted.eu/articles/castprint-3d-printing-healthtech-startup-wise-guys-techchill-latvia.

* cited by examiner

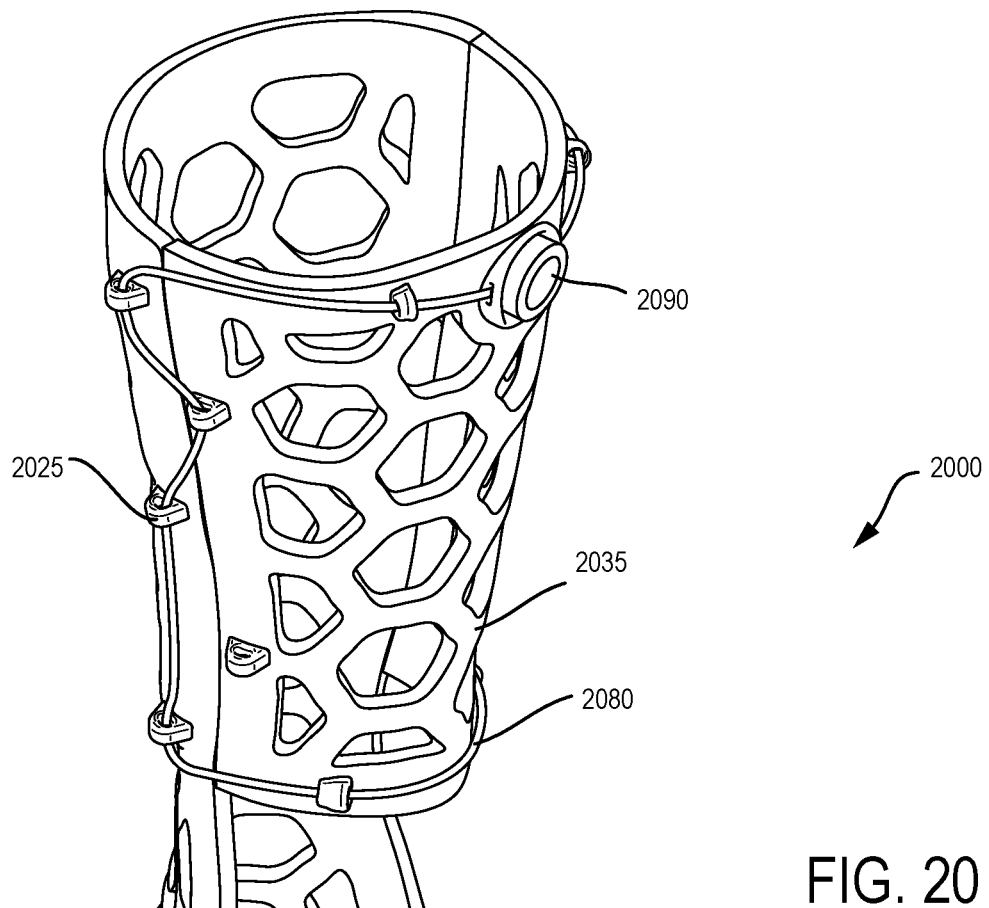
FIG. 20
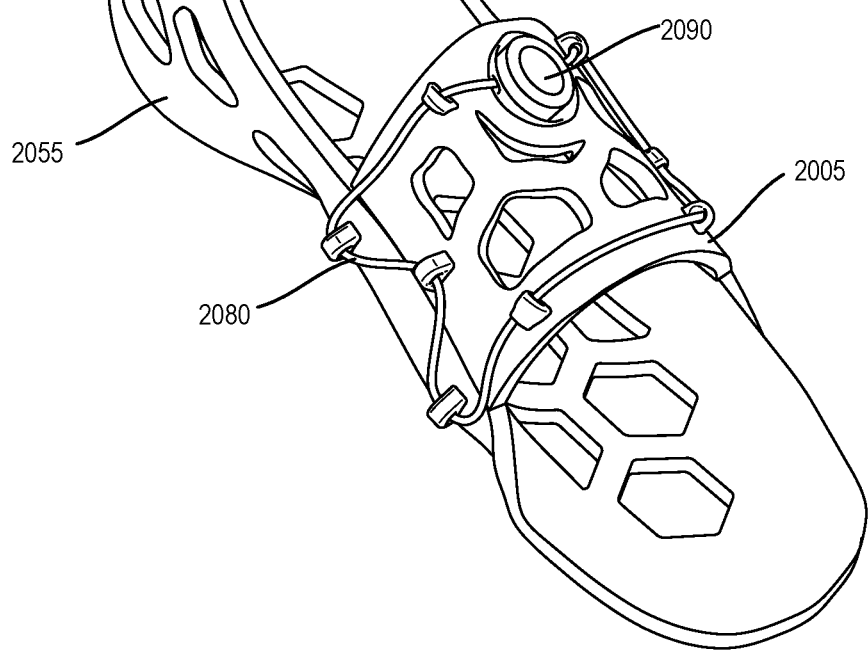

ADJUSTABLE BRACE AND PROCESSES FOR MAKING AND USING SAME

BACKGROUND

Bone fractures may occur as a result of mechanical impact or bone diseases. Orthopedic braces may be used for a patient to wear during the process of recovery and rehabilitation from such musculoskeletal injury or trauma, and they may be used to facilitate proper alignment, support, stabilization, and/or protection of certain parts of the body (e.g., muscles, joints, and bones) as they heal. Orthopedic braces are often recommended for restricting and assisting general movement, removing weight from healing or injured joints and muscles, correcting the shape and function to reduce pain and facilitate improved mobility, and aiding overall musculoskeletal rehabilitation. The body swells as it heals, and such swelling may fluctuate over time. As such, ensuring that an orthopedic brace can accommodate such fluctuations while maintaining relative patient comfort may be important to facilitate optimal healing. Current orthopedic braces, even those made of multiple components, do not address the aforementioned points.

As a result, there is a need for improved orthopedic braces and methods of producing and installing the same.

BRIEF SUMMARY OF THE DISCLOSURE

Briefly described, aspects of the present disclosure generally relate to adjustable orthopedic braces (herein referred to as an adjustable brace) for improved healing and comfort, and processes for making and using the same.

According to a first aspect, the present disclosure relates to an adjustable brace comprising: (i) a first 3D printed stabilizer comprising a first exterior surface, a first interior surface, and a first thickness; (ii) a second 3D printed stabilizer comprising a second exterior surface, a second interior surface, and a second thickness; (iii) one or more attachment points; and (iv) one or more selective engagement structures, wherein: the first 3D printed stabilizer selectively engages with the second 3D printed stabilizer at common peripheries of the first 3D printed stabilizer and second 3D printed stabilizer via the one or more selective engagement structures, respectively; and a position of the first 3D printed stabilizer is adjustable in relation to the second 3D printed stabilizer.

According to a second aspect, the adjustable brace of the first aspect or any other aspect, wherein the one or more selective engagement structures comprise one or more tabs.

According to a third aspect, the adjustable brace of the second aspect or any other aspect, wherein the one or more selective engagement structures comprise one or more recesses.

According to a fourth aspect, the adjustable brace of the third aspect or any other aspect, wherein the position of the first 3D printed stabilizer is adjustable in relation to the second 3D printed stabilizer at a particular distance.

According to a fifth aspect, the adjustable brace of the fourth aspect or any other aspect, wherein the particular distance is based at least in part on a length of the one or more tabs.

According to a sixth aspect, the adjustable brace of the fifth aspect or any other aspect, wherein at least one flexible lacing member extends along a first stabilizer guide and a second stabilizer guide; and the flexible lacing member adjustably secures the first 3D printed stabilizer to the second 3D printed stabilizer.

According to a seventh aspect, the adjustable brace of the sixth aspect or any other aspect, comprising at least one closure mechanism coupled to the one or more attachment points, the at least one closure mechanism comprising a spool and a control for selectively winding a length of the flexible lacing member around the spool to loosen or tighten the first 3D printed stabilizer and the second 3D printed stabilizer around the body part.

According to an eighth aspect, the adjustable brace of the seventh aspect or any other aspect, wherein selectively winding the length of the flexible lacing member around the spool loosens or tightens the first 3D printed stabilizer and the second 3D printed stabilizer around the body part thereby adjusting the position of the first 3D printed stabilizer in relation to the second 3D printed stabilizer the particular distance.

According to a ninth aspect, the adjustable brace of the eighth aspect or any other aspect, wherein the spool comprises: a periphery; and a plurality of ratchet teeth disposed around the periphery, the ratchet teeth configured to selectively engage a pawl that inhibits rotation of the spool in one direction.

According to a tenth aspect, the adjustable brace of the ninth aspect or any other aspect, wherein the flexible lacing member is removably attached to the spool such that the lacing member may be removed from the closure mechanism without removing the spool.

According to an eleventh aspect, the adjustable brace of the tenth aspect or any other aspect, wherein the first exterior surface forms the one or more attachment points.

According to a twelfth aspect, the adjustable brace of the tenth aspect or any other aspect, wherein the second exterior surface forms the one or more attachment points.

According to a thirteenth aspect, the adjustable brace of the first aspect or any other aspect, wherein at least a portion of the first 3D printed stabilizer is made of resilient material.

According to a fourteenth aspect, the adjustable brace of the first aspect or any other aspect, wherein at least a portion of the second 3D printed stabilizer is made of resilient material.

According to a fifteenth aspect, the adjustable brace of the first aspect or any other aspect, wherein a first resilient cushion member extends from the first interior surface.

According to a sixteenth aspect, the adjustable brace of the first aspect or any other aspect, wherein a second resilient cushion member extends from the second interior surface.

The present disclosure also relates to an adjustable brace comprising, according to a seventeenth aspect: (i) a plurality of stabilizers, each stabilizer having an exterior surface, an interior surface, a thickness, and a plurality of stabilizer guides; (ii) one or more attachment points; and (iii) one or more selective engagement structures, wherein: a first stabilizer of the plurality of stabilizers selectively engages with a periphery of a second stabilizer of the plurality of stabilizers; and wherein a position of the first stabilizer is adjustable in relation to at least one stabilizer of the plurality of stabilizers.

According to an eighteenth aspect, the adjustable brace of the seventeenth aspect or any other aspect, wherein the at least one stabilizer is the second stabilizer.

According to a nineteenth aspect, the adjustable brace of the eighteenth aspect or any other aspect, wherein at least one flexible lacing member extends along the stabilizer guides, and wherein the at least one flexible lacing member adjustably secures the first stabilizer to the at least one stabilizer.

According to a twentieth aspect, the adjustable brace of the nineteenth aspect or any other aspect, further comprising at least one closure mechanism coupled to a particular attachment point of the one or more attachment points, the at least one closure mechanism including a spool and a control for selectively winding a length of the at least one flexible lacing member around the spool to loosen and tighten the adjustable brace around the body part.

According to a twenty-first aspect, the adjustable brace of the twentieth aspect or any other aspect, wherein the spool has a periphery and includes a plurality of ratchet teeth disposed around the periphery, the ratchet teeth configured to selectively engage a pawl that inhibits rotation of the spool in one direction.

According to a twenty-second aspect, the adjustable brace of the twentieth aspect or any other aspect, wherein the at least one flexible lacing member is removably attached to the spool such that the at least one flexible lacing member may be removed from the at least one closure mechanism without removing the spool.

According to a twenty-third aspect, the adjustable brace of the twentieth aspect or any other aspect, wherein one or more stabilizers of the plurality of stabilizers further includes the one or more selective engagement structures in the form of tabs.

According to a twenty-fourth aspect, the adjustable brace of the twenty-third aspect or any other aspect, wherein the one or more stabilizers further includes the one or more selective engagement structures in the form of recesses.

According to a twenty-fifth aspect, the adjustable brace of the twenty-fourth aspect or any other aspect, wherein the one or more attachment points is on the one or more stabilizers.

According to a twenty-sixth aspect, the adjustable brace of the twenty-fifth aspect or any other aspect, wherein the one or more stabilizers is 3D printed based on patient-specific anatomy.

According to a twenty-seventh aspect, the adjustable brace of the twenty-sixth aspect or any other aspect, wherein at least a portion of the one or more stabilizers is made of resilient material.

The present disclosure also relates to method of fabricating an adjustable brace for stabilizing a body part, according to a twenty-eighth aspect, comprising the steps of: (i) scanning the body part; (ii) generating a patient-specific three-dimensional digital model of the body part based on the scan; (iii) designing a patient-specific adjustable brace based on the digital model of the body part, the adjustable brace comprising: a first stabilizer having a first exterior surface, a first interior surface, and a first thickness; the first stabilizer further including a plurality of first stabilizer guides and one or more tabs; a second stabilizer comprising a second exterior surface, a second interior surface, and a second thickness; the second stabilizer further including a plurality of second stabilizer guides and one or more recesses; and a closure mechanism attached to the first stabilizer, the closure mechanism including a control; (iii) instructing a 3D printer to generate the patient-specific adjustable brace; (iv) placing the first stabilizer on a first side of the body part; (v) placing the second stabilizer in contact with the first stabilizer and on a second side of the body part; (vi) inserting the tabs into the recesses; (vii) lacing at least one flexible lacing member through the first and second stabilizer guides, wherein the flexible lacing member connects to the closure mechanism to flexibly secure the first stabilizer to the second stabilizer; and (viii) adjusting the closure mechanism using the control selectively adjust a tightness of the flexible lacing member, wherein the adjustable brace is loosened and tightened around the patient body part.

BRIEF DESCRIPTION OF THE DRAWINGS

FIG. 20 is a perspective view of one embodiment of an assembled leg brace with closure mechanism in accordance with the principles of this disclosure.

DETAILED DESCRIPTION

Figure 1:
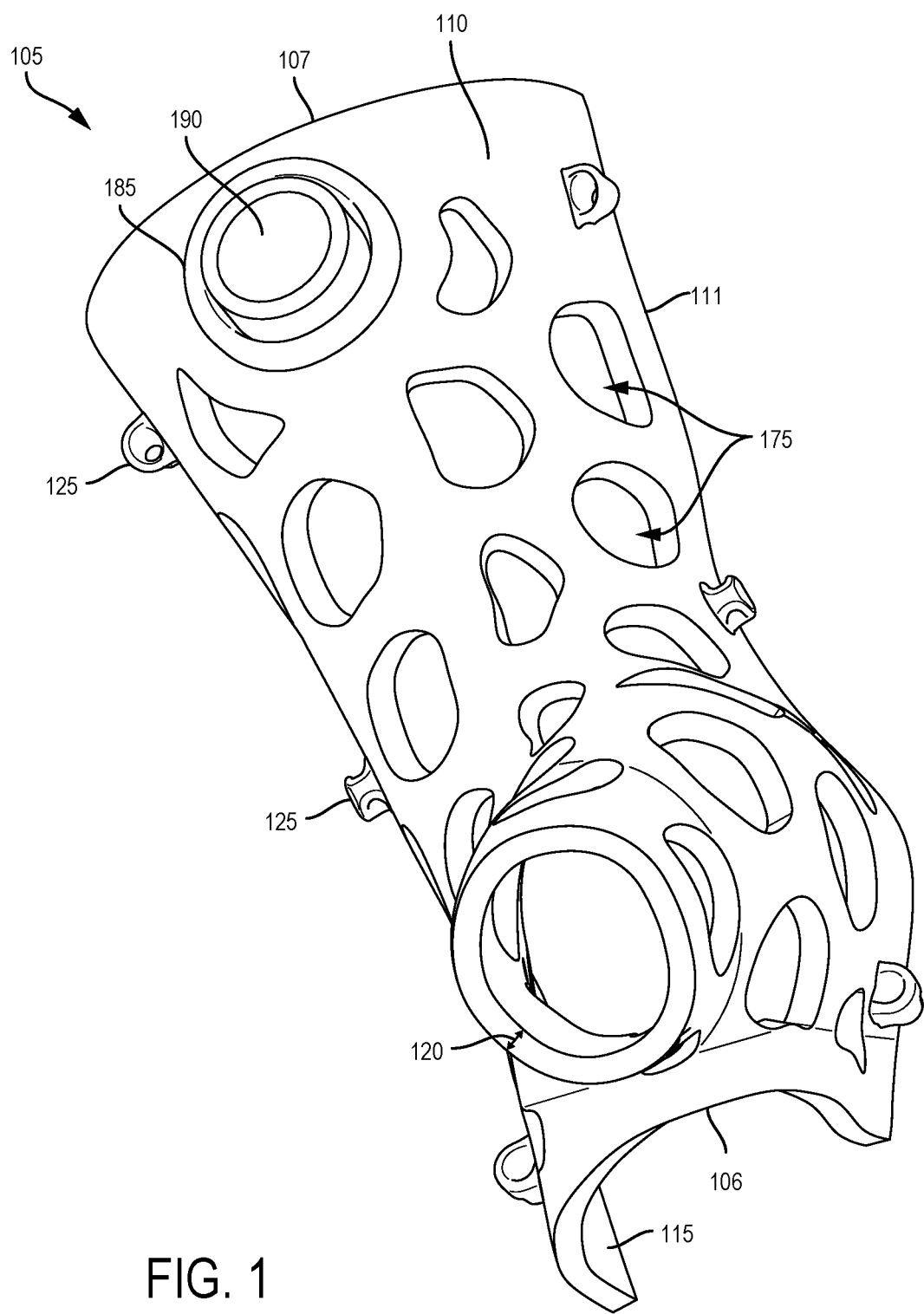
FIG. 1 is a perspective view of one embodiment of a first stabilizer for an adjustable brace in accordance with the principles of this disclosure.

This disclosure relates to braces for supporting orthopedic injuries. In particular, this disclosure relates to an adjustable brace that may adjust in size to account for changes in swelling during the healing process of an orthopedic injury.

For example, in the case of a lower extremity injury, the leg may fluctuate in circumference by 30 mm or more over a relatively short period of time. Existing braces including plaster casts do not adjust in size, which may cause pain or discomfort if swelling increases, and may provide insufficient support if the swelling decreases more than expected. As such, there is a need for a stabilizing brace that can easily adjust to accommodate such changes in the size of a patient's anatomy as it heals.

In at least one embodiment, the adjustable brace includes one or more parts, heretofore referred to as "stabilizers", that when assembled enclose and stabilize a portion of patient anatomy. The stabilizers are adjustable in relation to each other such that the tightness or looseness of the overall brace may be varied. In some embodiments, the adjustable brace includes an adjustable closure mechanism combined with engagement structures (e.g., male structures, such as tabs) disposed along the peripheries of one stabilizer, and complementary engagement structures (e.g., female structures, such as recesses) disposed along the peripheries of another stabilizer. For example, an adjustable brace for the leg may extend proximal to the knee and include rectangularly-shaped engagement structures with filleted edges while an adjustable brace for the arm may extend proximal to the elbow and may include ellipsoid-shaped engagement structures. The engagement structures may be 3D-printed and integrally formed with one stabilizer, or may be manufactured separately and then coupled to one stabilizer (e.g., metal pins coupled to one stabilizer and inserted into the complementary engagement structures of another stabilizer). The engagement structures of each stabilizer may be on the same three-dimensional plane in order to reduce friction and simplify assembly and/or disassembly of the adjustable brace. Selectively adjusting the closure mechanism tightens or loosens the adjustable brace around a patient body part, thereby allowing the rigid stabilizers to accommodate swelling without sacrificing the integrity of the overall brace.

As used herein, "patient-specific" means a part or component is custom-made for a particular patient using a variety of manufacturing techniques including, but not limited to, 3D printing, injection molding, or milling, amongst other techniques. Generally speaking, such patient-specific manufacturing techniques involve scanning or creating a mold of patient anatomy, creating a 3D model of a device that is specific to patient needs, and then manufacturing the device. In some embodiments, one or more stabilizers may be at least partially additively manufactured according to patient-specific design needs and with the aforementioned features. Exemplary materials may be of relatively high flexural strength with a flexural modulus of at least 1500 MPa. Exemplary materials may also be biocompatible and/or waterproof, and may include, but are not limited to, various medical grade or otherwise suitable materials such as plaster and plastic (e.g., polypropylene-like plastics, thermosetting plastics, etc.). In alternative embodiments, one or more of the stabilizers may include more than one material composition.

The above features (and others) will be discussed herein in the context a forearm brace. However, it will be understood that the concepts discussed here are applicable to any suitable brace (e.g., knee, elbow, neck, spine, etc.) used to support any human (or animal) anatomy.

Referring now to FIG. 1, one embodiment of an exemplary first stabilizer 105 of an exemplary adjustable brace in accordance with the principles of the present disclosure is shown. In this embodiment, the first stabilizer 105 may be aligned with and stabilize a patient radius bone. The first stabilizer 105 includes a first end 106 which may conform to the contour of a patient hand and thumb, and a second end 107 which may conform to the contour of a patient forearm. The first stabilizer 105 also includes an exterior surface 110 and an interior surface 115, each containing additional features discussed herein.

According to at least one embodiment, the first stabilizer 105 may include at least one ventilation hole 175 that extends from any suitable area of the exterior surface 110 through to the interior surface 115. Each ventilation hole 175 may form a circular, ovular, or any other suitable shape, and may each have an opening between 10 mm and 50 mm. The ventilation holes 175 may be uniform in shape and size or may vary in shape and size according to patient needs. Similarly, the ventilation holes 175 may form an overall surface pattern of regular or irregular nature. Such a pattern may be beneficial for hygienic purposes (e.g., reducing the risk of cutaneous complications), wearing comfort (e.g., reducing the risk of bone/joint injuries), and accommodation of swelling fluctuation as healing progresses. Furthermore, inclusion of one or more ventilation holes 175 may reduce material usage, thus yielding a lighter and more ergonomic overall assembled brace.

Figure 7:
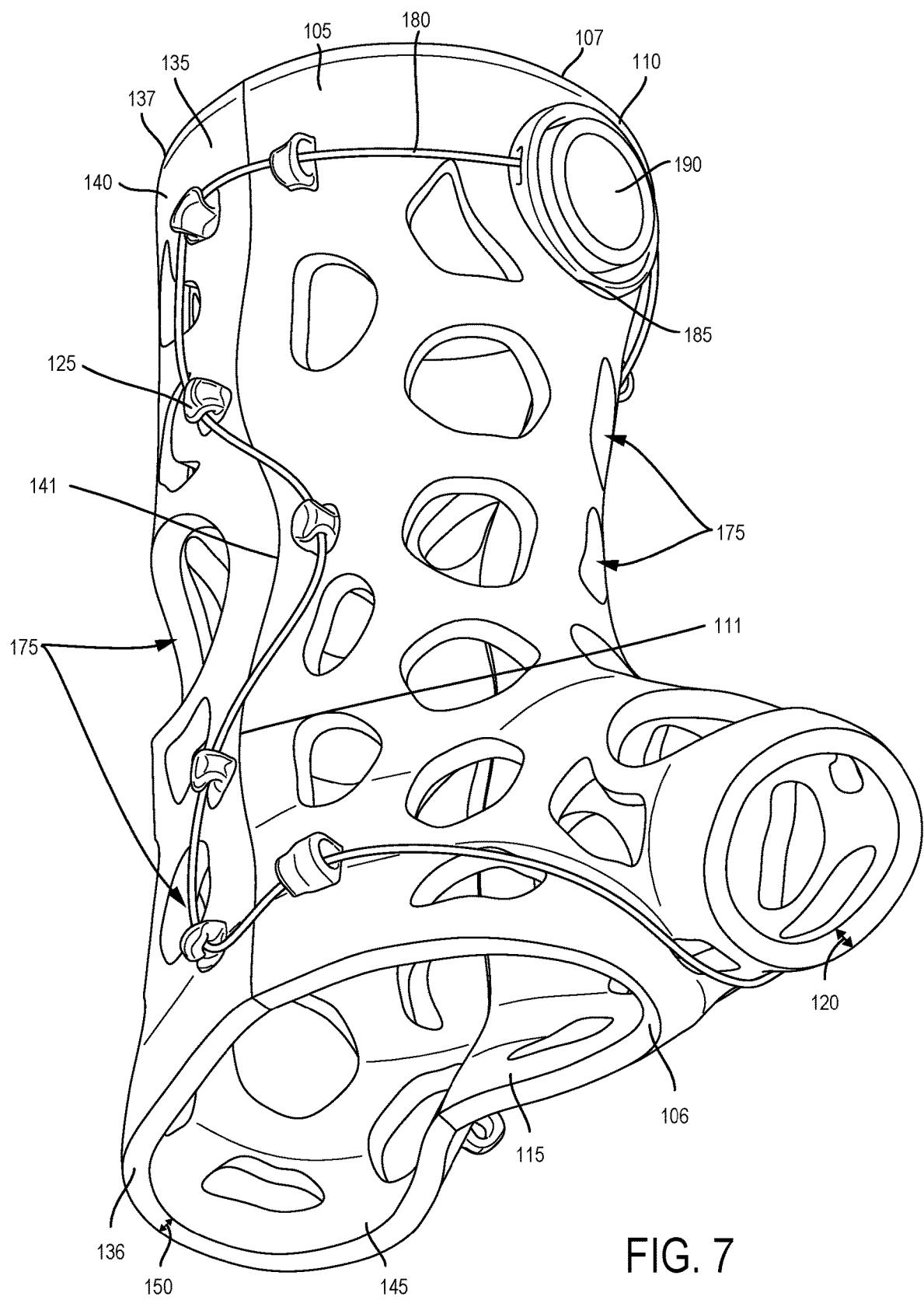
FIG. 7 is a perspective view of one embodiment of an assembled adjustable brace (constructed from the first stabilizer of FIG. 1 and second stabilizer of FIG. 4), in accordance with the principles of this disclosure.

The exterior surface 110 may further include one or more guides 125 positioned along one or more edges 111. In some embodiments, the guides 125 may be eyelets (e.g., punched eyelets, webbed eyelets, etc.), D-Rings, hooks or any other suitable structure or combination of structures thereof, and may have an average radius between 3 mm and 5 mm. The guides 125 may be evenly spaced apart, such as every 10 mm, 15 mm, 20 mm, 25 mm, 30 mm, 50 mm, 75 mm, 100 mm, or any other suitable distance apart. In other embodiments, the guides 125 may be spaced according to patient-specific needs (such as at irregular intervals). As shown in FIG. 7, one or more flexible lacing members 180 may be threaded through, around, or along one or more guides 125, and the exterior surface 110 may additionally include an attachment point 185 upon which a closure mechanism 190 may be attached.

Figure 2:
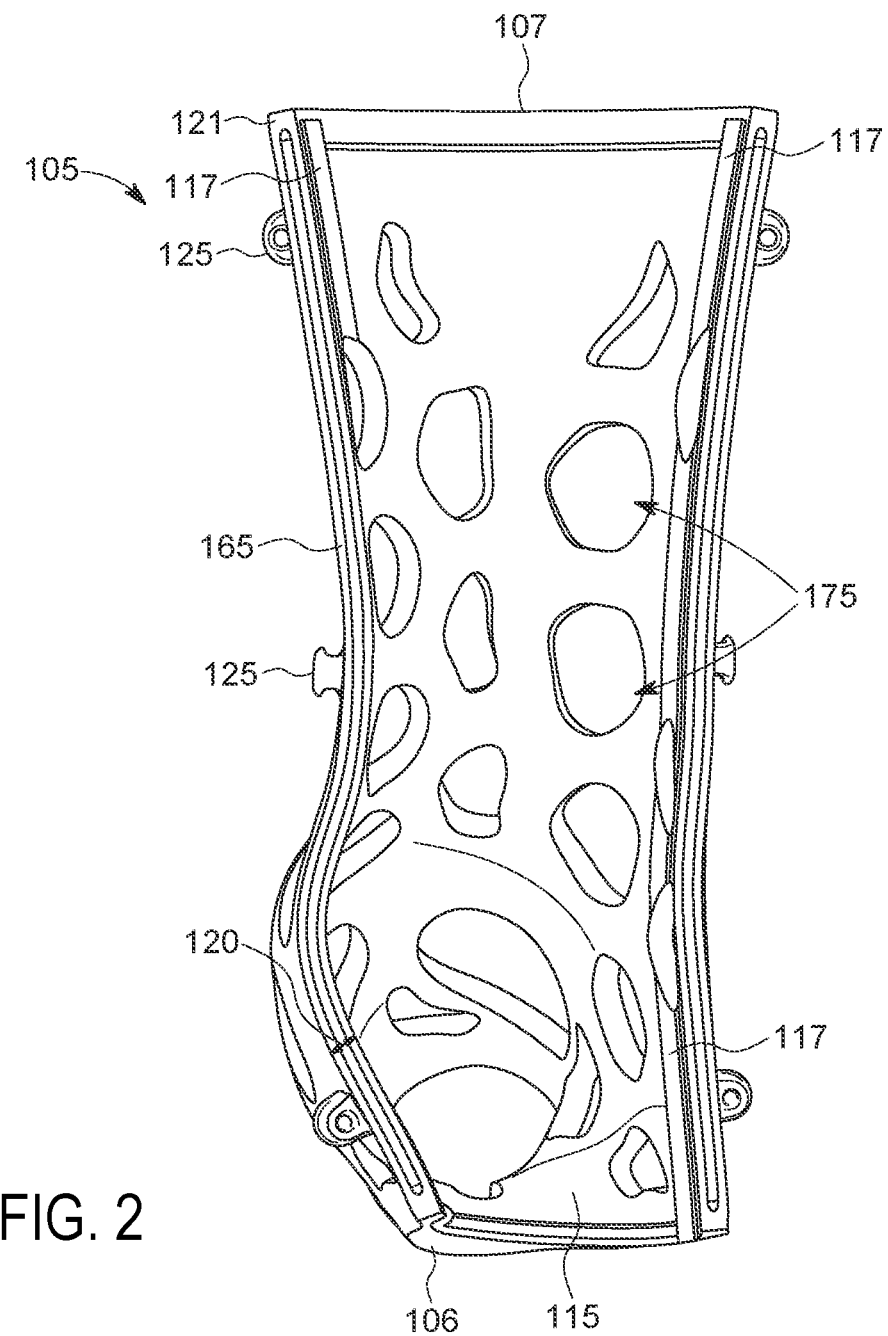
FIG. 2 is another perspective view of the first stabilizer of FIG. 1.

Referring now to FIG. 2, the interior surface 115 may conform to patient-specific needs and dimensions, resulting in a thickness 120 that may vary between 2 mm and 10 mm in order to provide localized variations in flexural strength. In some embodiments, the thickness 120 may be 4 mm, while in other embodiments the thickness 120 may be 5 mm. In general, the thickness 120 may increase or decrease where variable flexural strength is desired for the first stabilizer 105. Alternatively, the thickness 120 may remain consistent while flexural strength varies when multiple materials are used. For example, height, length, and/or width may be based on the patient-specific nature of the braces of the present disclosure; thus, a circumference of the interior of the brace may correlate to the circumference of the 3D scanned patient anatomy.

In certain embodiments, engagement structures 165 may extend from one or more peripheries 121. The engagement structures 165, here shown as tabs, selectively engage with complementary engagement structures 170 (shown in FIG. 5) on one or more additional stabilizers, which align and secure the stabilizers with respect to each other. Although tabs are shown in the present embodiment, other embodiments may include any suitable structure to assist in brace assembly—including, but not limited to, pins, rods, or other fixtures. In some embodiments, the peripheries 121 may include an alternating pattern of both tabs and recesses that may selectively engage with complementary patterns of tabs and recesses on one or more additional stabilizers. In additional embodiments, the interior surface 115 may further include one or more resilient cushion members 117 that may improve patient comfort, although such cushion members may be unnecessary in certain embodiments where the first stabilizer 105 is patient specific. The resilient cushion members 117 may be in the form of padding, lining, foam, or any other suitable material.

Figure 3:
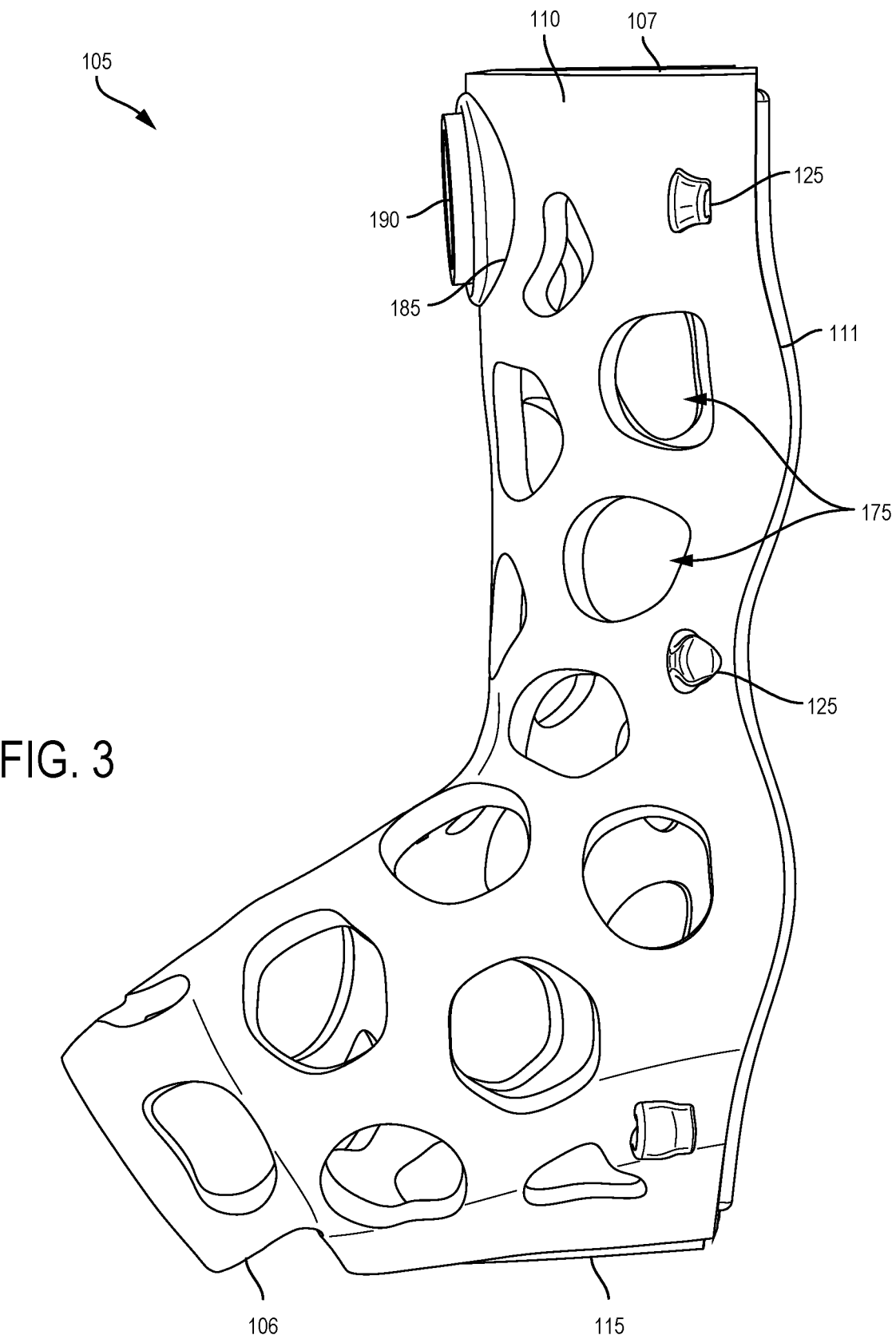
FIG. 3 is a side exterior view of the first stabilizer of FIG. 1.

FIG. 3 is a side view of the first stabilizer 105, showing a pattern of ventilation holes 175, spacing of guides 125, and overall patient conforming shape. As shown, first stabilizer 105 is contoured to conform to a patient hand and forearm. The peripheries 121 are contoured such that the first stabilizer 105 may be secured to one or more additional stabilizers. In this embodiment, the peripheries 121 have a generally curved shape, but other embodiments may include peripheries 121 of any suitable shape (e.g., zig-zag, straight, sinusoidal, etc.). Engagement structures 165, in this embodiment shown as tabs, protrude from the peripheries 121 at a height of 2 to 15 mm and a thickness of 0.5 to 10 mm. In some embodiments, the engagement structures 165 may protrude at a height of 10 to 25 mm. In certain embodiments, the tabs 165 may have a rectangular or any other suitable cross-sectional shape. The tabs 165 may extend continuously along the full length of the peripheries 121, such as in this embodiment, or the tabs 165 may extend intermittently according to other embodiments. Furthermore, the tabs 165 may be partially or fully flexible, or partially or fully rigid, or vary in flexural strength according to patient-specific needs.

Figure 4:
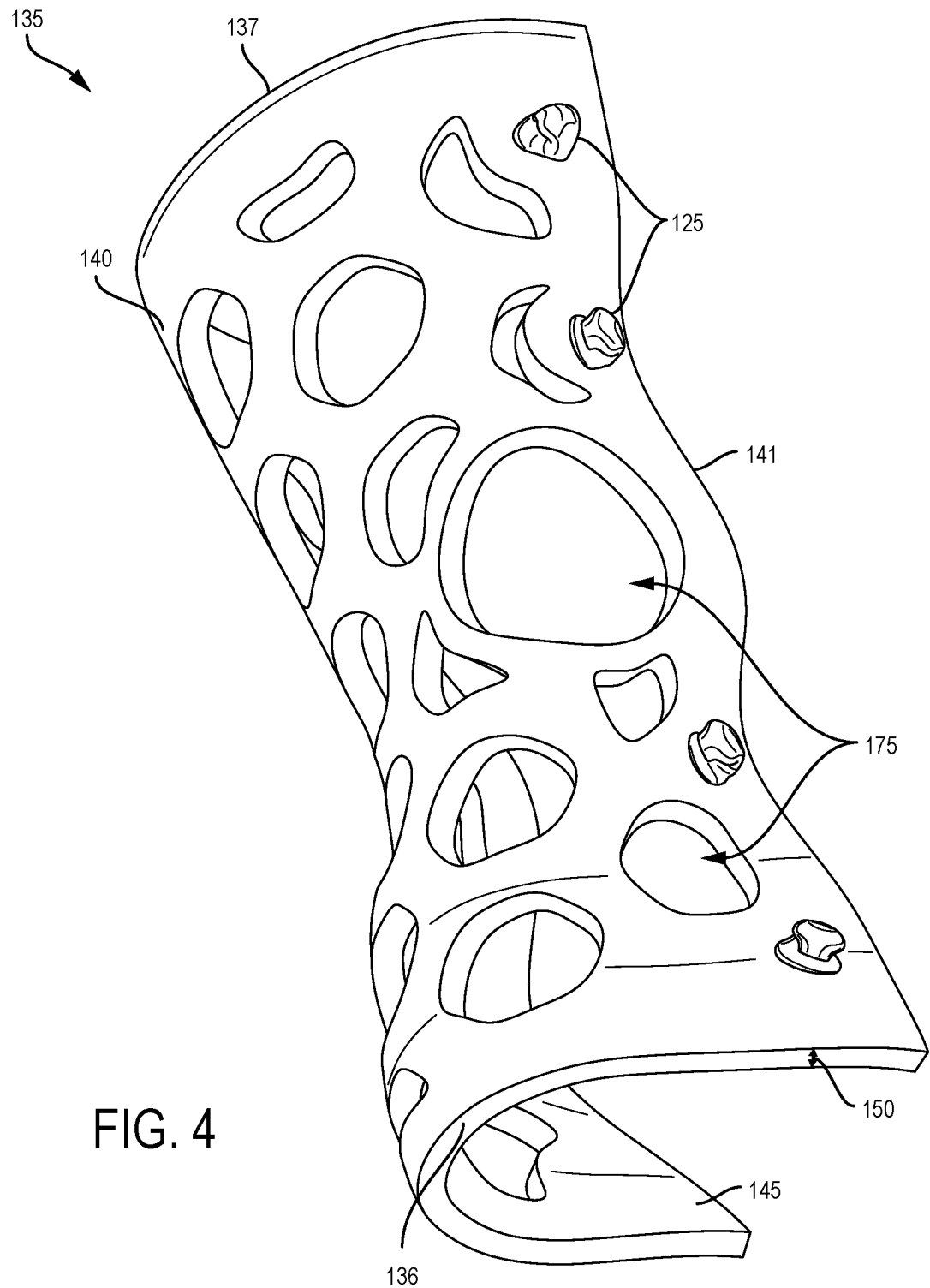
FIG. 4 is a perspective view of one embodiment of a second stabilizer for an adjustable brace in accordance with the principles of this disclosure.

Turning now to FIG. 4, an exemplary second stabilizer 135 of an exemplary adjustable brace in accordance with the present disclosure is shown. In this embodiment, the second stabilizer 135 may be aligned with and stabilize a patient's ulna bone. The second stabilizer 135 includes a first end 136, which may conform to the contour of a patient's hand, and a second end 137 which may conform to the contour of the patient's forearm. The second stabilizer 135 also includes an exterior surface 140 and an interior surface 145, each containing additional features discussed herein.

According to at least one embodiment, the second stabilizer 135 may include at least one ventilation hole 175 that extends from any suitable area of the exterior surface 140 through to the interior surface 145. Each ventilation hole 175 may form a circular, ovular, or any other suitable shape, and may each have a radius between 10 mm and 50 mm. The ventilation holes 175 may be uniform in shape and size, or may vary in shape and size according to patient needs. Similarly, the ventilation holes 175 may form an overall surface pattern of regular or irregular nature. Such a pattern may be beneficial for hygienic purposes (e.g., reducing the risk of cutaneous complications), wearing comfort (e.g., reducing the risk of bone/joint injuries), and accommodation of swelling fluctuation as healing progresses. Furthermore, inclusion of one or more ventilation holes 175 may reduce material usage, thus yielding a lighter and more ergonomic overall assembled brace.

The exterior surface 140 may further include one or more guides 125 positioned along one or more edges 141. In some embodiments, the guides 125 may be eyelets (e.g., punched eyelets, webbed eyelets, etc.), D-Rings, hooks or any other suitable shape or combination of structures thereof, and may have an average radius between 3 mm and 5 mm. The guides 125 may be evenly spaced apart, such as every 10 mm, 15 mm, 20 mm, 25 mm, 30 mm, 50 mm, 75 mm, 100 mm, or any other suitable distance apart. In other embodiments, the guides 125 may be positioned according to patient-specific needs (such as at irregular intervals). As shown in FIG. 7, one or more flexible lacing members 180 may be threaded through one or more guides 125.

Figure 5:
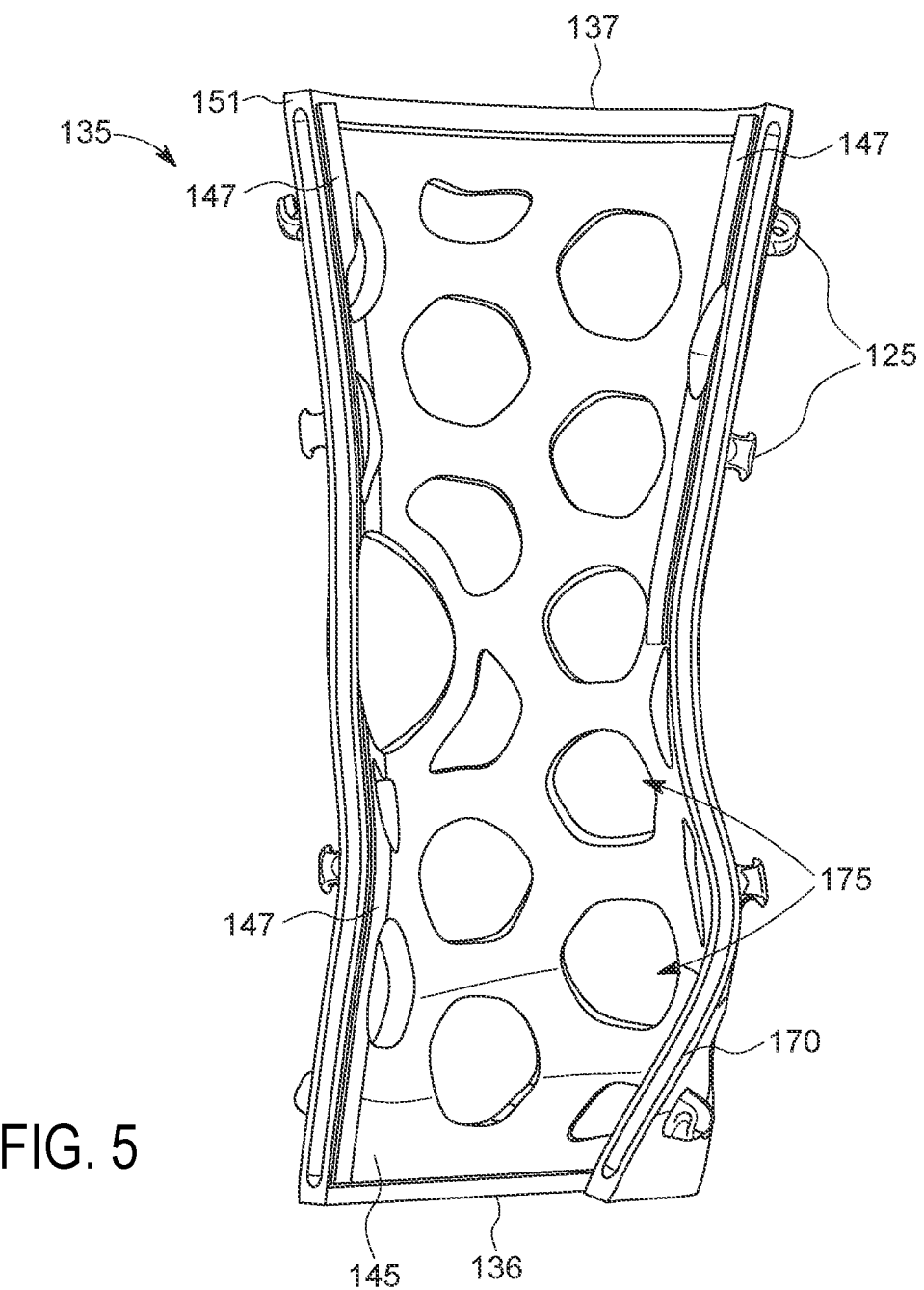
FIG. 5 is another perspective view of the second stabilizer of FIG. 4.

Referring now to FIG. 5, the interior surface 145 may conform to patient-specific needs and dimensions. The second stabilizer 135 has a thickness 150 that may vary between 2 mm and 10 mm to provide variable flexural strength. In some embodiments, the thickness 150 may be 4 mm, while in other embodiments the thickness 150 may be 5 mm. In general, the thickness 150 may increase or decrease where variable flexural strength is desired for the second stabilizer 135. Alternatively, the thickness 150 may remain consistent while flexural strength varies when multiple materials are used. Dimensions such as height, length, and/or width may be based on the patient-specific nature of the braces of the present disclosure.

As shown in FIG. 5, one or more peripheries 151 may include one or more complementary engagement structures 170, here shown as recesses, extending along the peripheries 151. Tabs of the first stabilizer (shown in FIG. 2) selectively engage with recesses 170 of the second stabilizer 135, which aligns and secures the stabilizers with respect to each other. Although recesses 170 are shown in the present embodiment, other embodiments may include any suitable complementary engagement structure (e.g., slots, hinges, etc.) to assist in brace assembly. In some embodiments, the peripheries 151 may include an alternating pattern of both tabs and recesses that may selectively engage with complementary patterns of tabs and recesses on one or more additional stabilizers. In additional embodiments, the interior surface 145 may further include at least one resilient cushion member 147 that may improve patient comfort, although such cushion members may be unnecessary in certain embodiments where the second stabilizer 135 is patient-specific. The resilient cushion member 147 may be in the form of padding, lining, foam, or any other suitable material.

Figure 6:
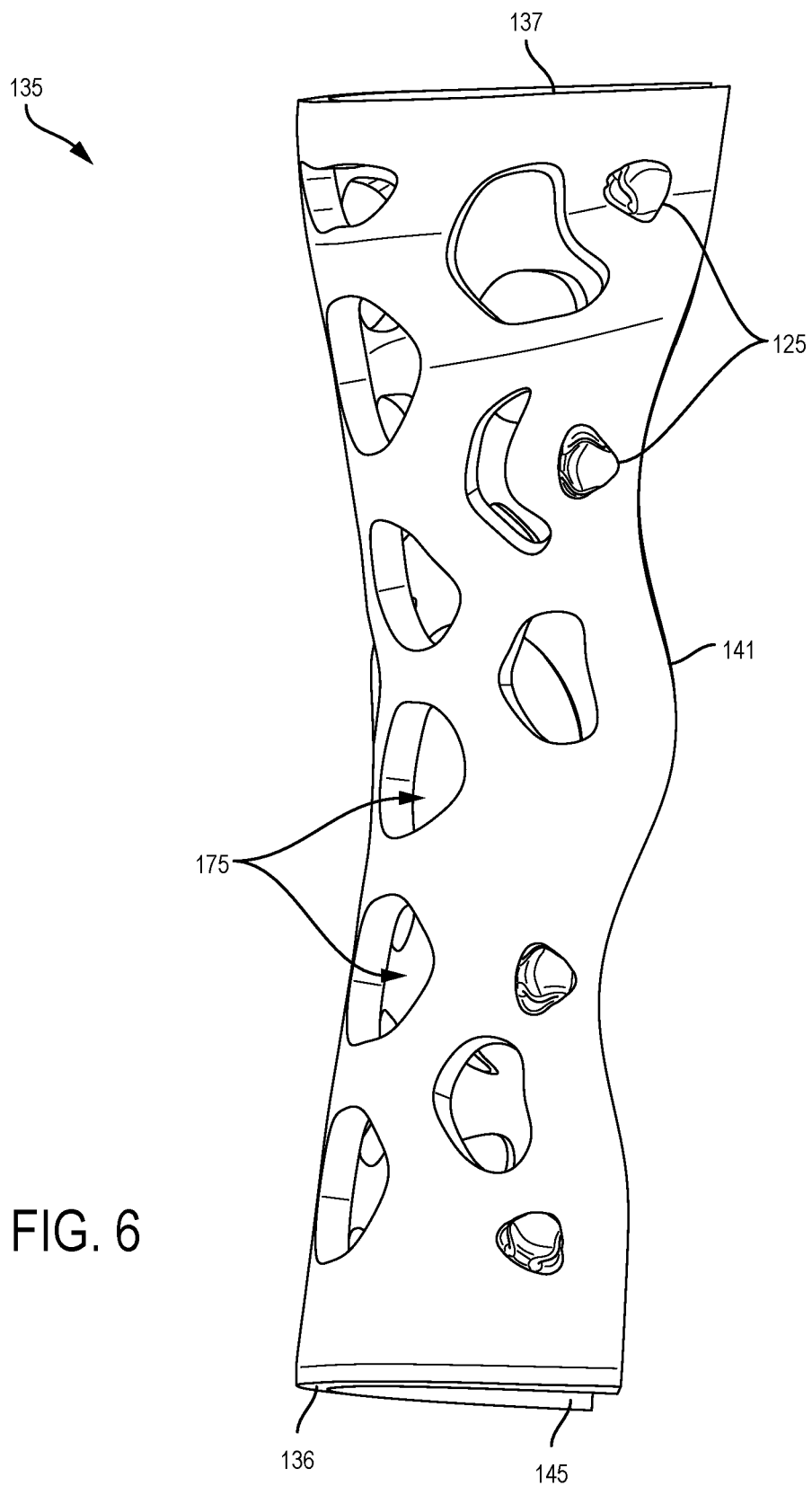
FIG. 6 is a side exterior view of the second stabilizer of FIG. 4.

FIG. 6 offers a side view of the second stabilizer 135, showing a pattern of ventilation holes 175, spacing of guides 125, and general patient conforming shape. The shape of the second stabilizer 135 is contoured to conform to a patient hand and forearm. The peripheries 151 are contoured such that the second stabilizer 135 may be secured to one or more additional stabilizers. In this embodiment, the peripheries 151 have a generally curved shape, but other embodiments may include peripheries 151 of any suitable shape (e.g., zig-zag, straight, sinusoidal, etc.). Complementary engagement structures 170, shown as recesses in FIG. 5, recede into the peripheries 151 at a depth of 2 to 15 mm, a width of 0.5 to 15 mm, and have a rectangular or any other suitable cross-sectional shape. In some embodiments, the complementary engagement structures 170 may recede at a depth of 10 to 25 mm. The complementary engagement structures 170 may extend continuously along the full length of the peripheries 151, such as in this embodiment, or the complementary engagement structures 170 may extend intermittently according to other embodiments. Furthermore, the complementary engagement structures 170 may be partially or fully flexible, or partially or fully rigid according to patient-specific needs.

Figure 9:
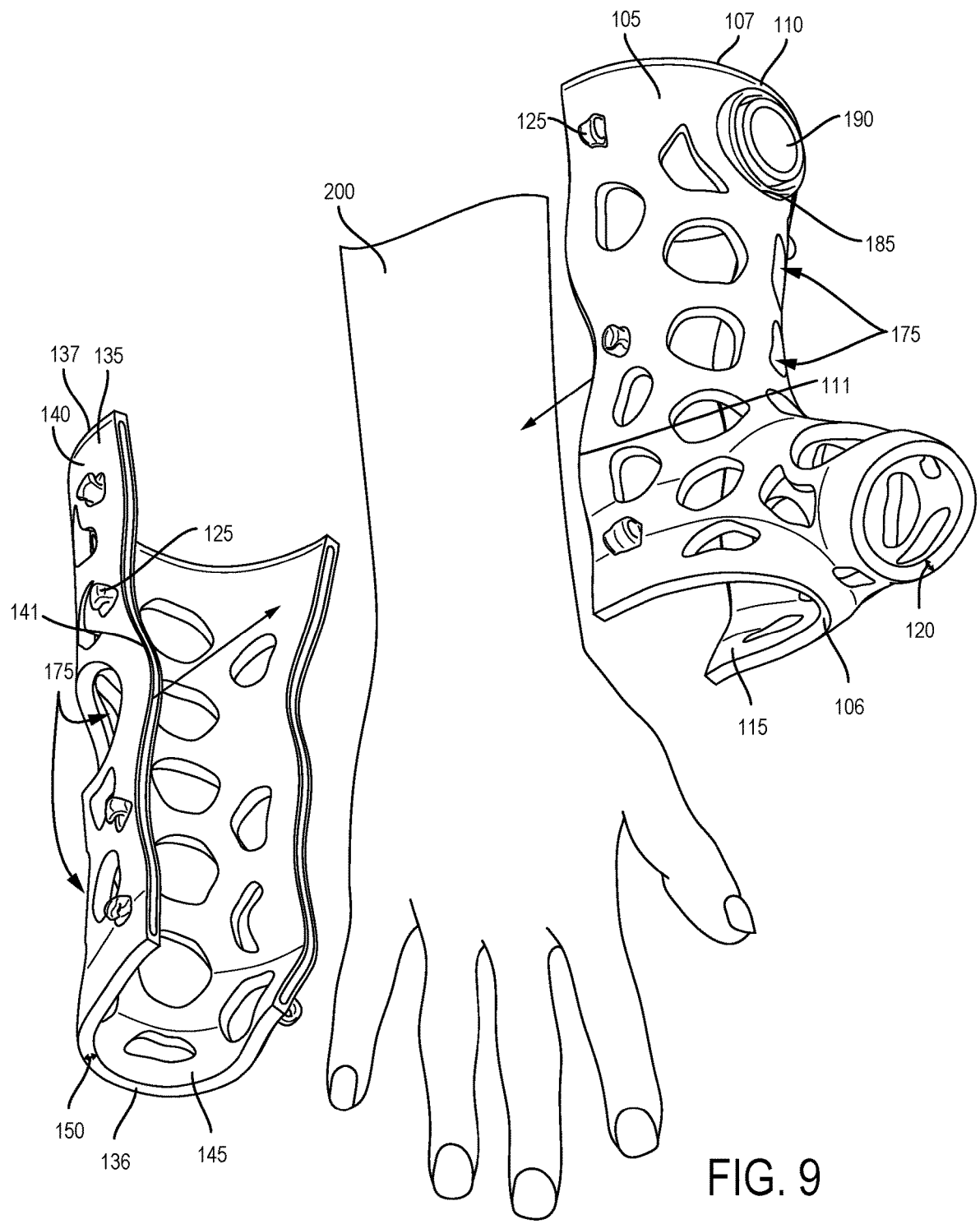
FIG. 9 is a view of a patient hand with the adjustable brace of FIG. 7 in an uninstalled position.

FIG. 7 shows one embodiment of an assembled adjustable brace 100 in accordance with the principles of this disclosure. The adjustable brace 100 includes the first stabilizer 105 of FIGS. 1-3 and the second stabilizer 135 of FIGS. 4-6. One or more flexible lacing members 180 (e.g., nylon string or polymer lacing) are laced along the stabilizer guides 125 such that the first stabilizer 105 is secured to the second stabilizer 135, but other embodiments may employ any other suitable structure such as VELCRO®, hooks, straps, etc. Furthermore, one or more engagement structures 165 (shown as tabs) of the first stabilizer 105 align with and selectively engage with one or more complementary engagement structures 170 (shown as recesses) of the second stabilizer 135. The selective engagement of tabs 165 and recesses 170 is shown in FIG. 9, wherein the tightness or looseness of the overall brace 100 may be adjusted in part by the tension of the flexible lacing members 180 (or any other suitable structure).

Figure 10:
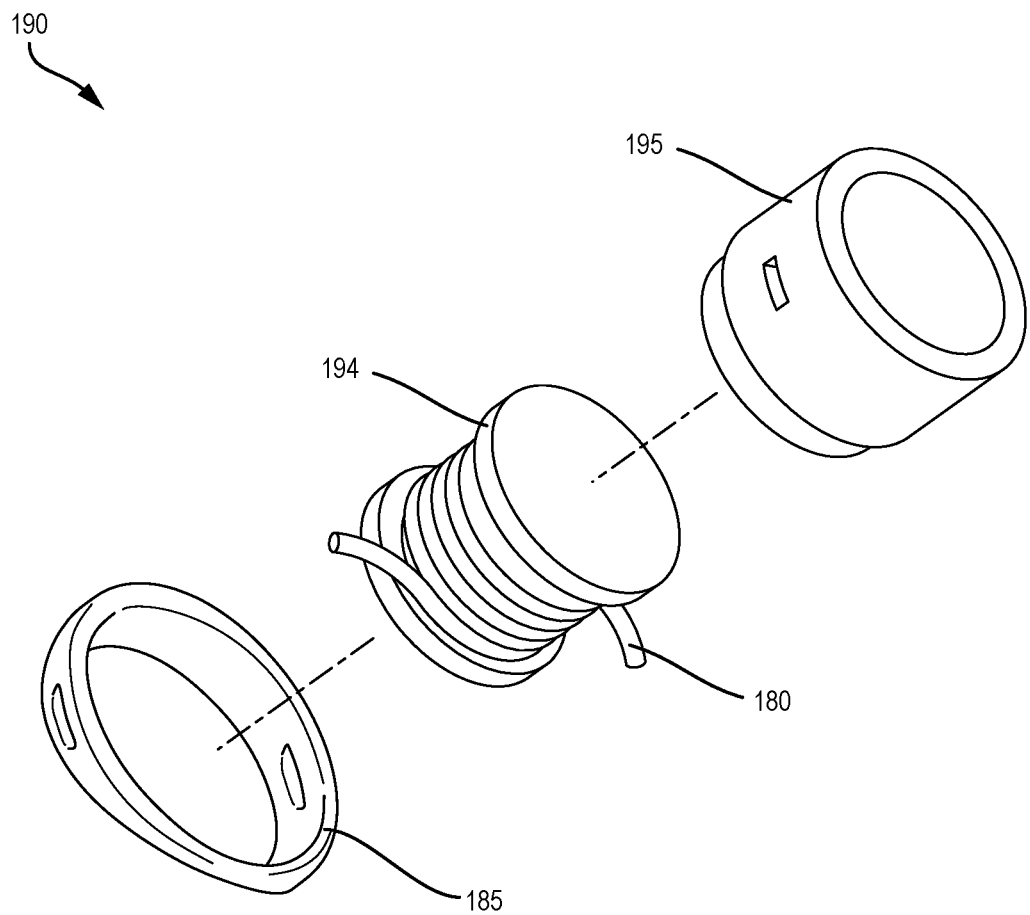
FIG. 10 is a view of one embodiment of a closure mechanism of the adjustable brace of FIG. 7.

In at least one embodiment, the adjustable brace 100 includes a closure mechanism 190. For example, the closure mechanism 190 may include a spool 194 and control 195 as shown in FIG. 10 (or any other suitable closure mechanism, such as a winch) for selectively winding a length of a flexible lacing member 180 around the spool 194 to loosen and tighten the adjustable brace 100 around the patient body part via adjusting the tension in the flexible lacing member 180. In some embodiments, the spool 194 may have a periphery including a plurality of ratchet teeth disposed around the periphery, wherein the ratchet teeth are configured to selectively engage a pawl that inhibits rotation of the spool 194 in one direction. In some embodiments, the flexible lacing member 180 of FIG. 7 may be removable from the closure mechanism 190 without removing any portion of the closure mechanism 190. Selective tightening and loosening of the adjustable brace 100 may improve wearer comfort, accommodate variations in swelling, and assist in injury recovery. Over time, the brace 100 may continue to be adjusted for desirable tightness or looseness.

Figure 8:
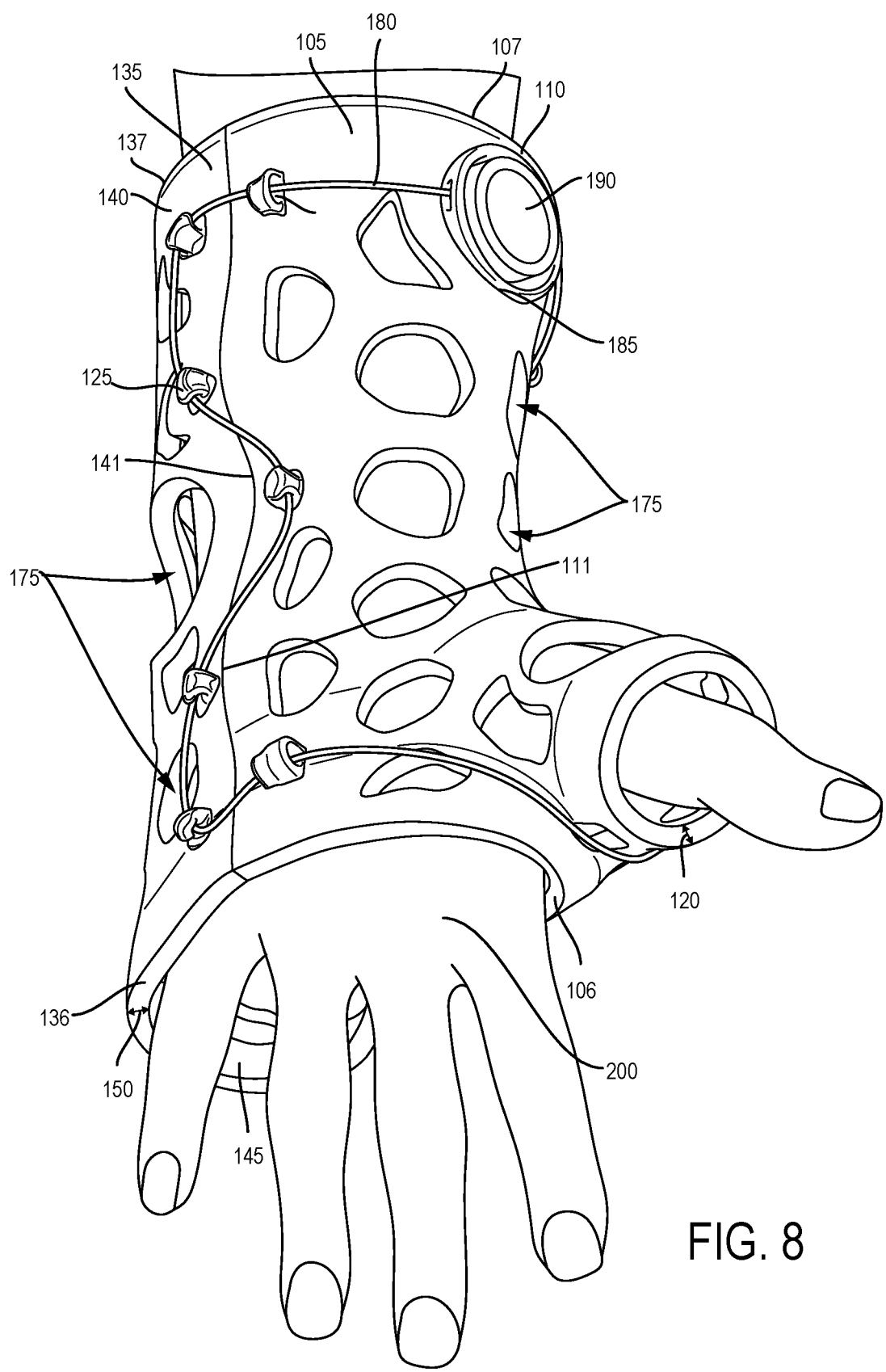
FIG. 8 is a view of a patient hand with the adjustable brace of FIG. 7 in an installed position.

With reference now to FIG. 8, a user may assemble the adjustable brace 100 by placing the patient hand through the first end 106 of the first stabilizer 105, and ensuring the placement of the forearm against the second end 107. The user may then place the second stabilizer 135 around the patient hand and forearm wherein the hand is fit through the first end 136 and the forearm is fit through the second end 137. The user may then adjust relative placement of the first 105 and second 135 stabilizers with respect to each other in order to properly align one or more engagement structures 165 (shown as tabs) disposed on peripheries 121 with one or more complementary engagement structures 170 (shown as recesses) disposed on peripheries 151. As shown in FIG. 9, the user may then engage the tabs 165 with the recesses 170, thereby removably attaching the first 105 and second 135 stabilizers. Turning back to FIG. 8, the user may then thread one or more flexible lacing members 180 along the guides 125 disposed on the first stabilizer edge 111 and the second stabilizer edge 141, and around the closure mechanism 190.

Figure 11:
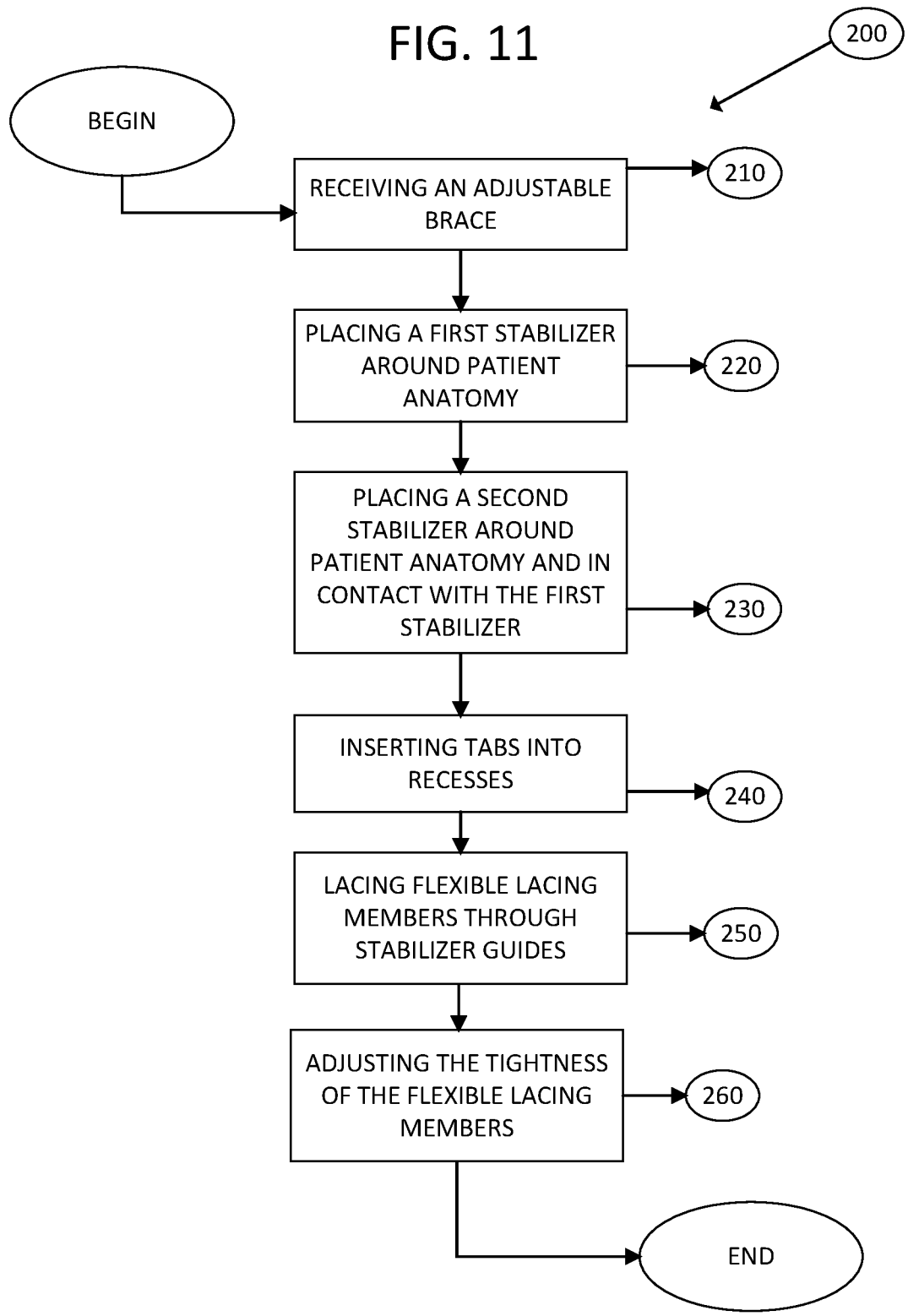
FIG. 11 is a flowchart of one embodiment of an adjustable brace assembly process, in accordance with the principles of this disclosure.

FIG. 11 shows one embodiment of a method 200 of using the adjustable brace 100 in accordance with the principles of this disclosure. The method 200 generally includes: (1) receiving an adjustable brace, the adjustable brace including one or more stabilizers 210; (2) placing a first stabilizer including one or more tabs on a first side of the patient anatomy 220; (3) placing a second stabilizer including one or more recesses in contact with the first stabilizer and on a second side of the patient anatomy 230; (4) inserting the tabs into the recesses 240; (5) lacing at least one flexible lacing member along a plurality of first and second stabilizer guides 250; and (6) selectively adjusting a tightness of the flexible lacing members around the stabilizer guides 260. In certain embodiments, the method of using adjustable brace 100 includes the step of using a control to selectively adjust the tightness of the flexible lacing members around the stabilizer guides.

Figure 12:
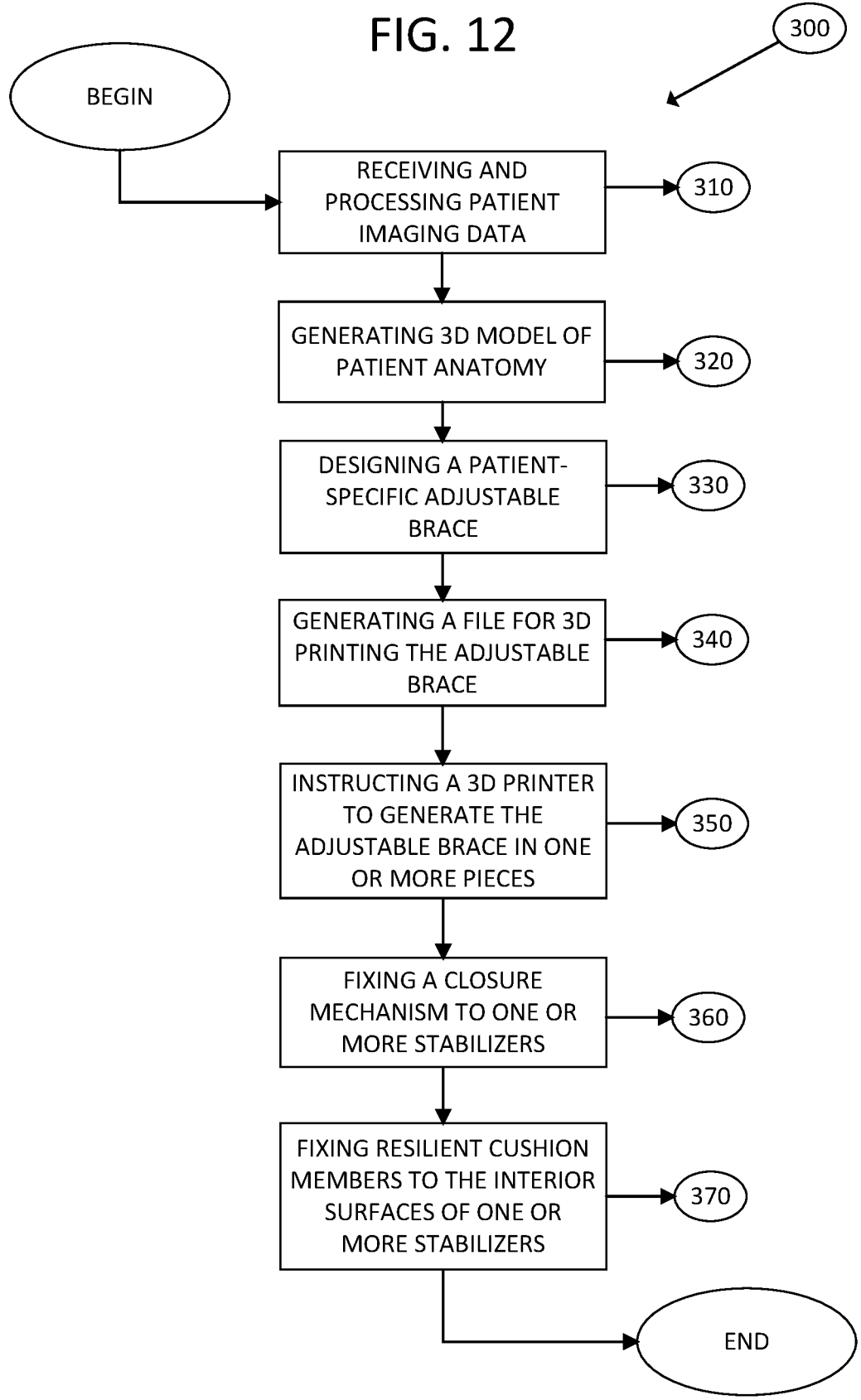
FIG. 12 is a flowchart of one embodiment of an adjustable brace manufacturing process in accordance with the principles of this disclosure.

Referring now to FIG. 12, in at least one embodiment, the adjustable brace is produced by 3D printing manufacturing methods. Process 300 generally includes: (1) receiving and processing patient imaging data 310; (2) generating a 3D model of a patient body part to be stabilized 320; (3) designing a patient-specific adjustable brace on the 3D model of the body part 330; (4) generating a file for 3D-printing the patient-specific adjustable brace based on the 3D model 340; and (5) instructing a 3D printer to generate the patient-specific adjustable brace in one or more pieces 350. Further manufacturing may include: (6) fixing a closure mechanism to one or more stabilizers 360; and (7) fixing one or more resilient cushion members to the interior surface of one or more stabilizers 370.

Although the embodiment shown herein is for a brace of the hand/wrist, the principles of this disclosure may extend to braces with any number and placement of stabilizers of any shape and size to stabilize any number and type of patient body parts. Various alternate embodiments are contemplated herein, such as, but not limited to, additional arm braces with different support structures for the hand and thumb, other upper extremity braces (e.g., full arm brace, shoulder brace, elbow brace, clavicle brace, etc.), lower extremity braces (e.g., foot brace, ankle brace, knee brace, hip brace, full leg brace, etc.), and braces for other anatomies (e.g., neck, spine, etc.). Alternative embodiments further include multiple adjustable braces in parallel and series that are adjustable with respect to each other such that adjustment may occur in one or more dimensions. Depending on patient-specific needs and patient anatomy type, any such alternative embodiment may include any suitable number of stabilizers of any suitable thicknesses, any suitable pattern and sizing of ventilation holes, any suitable number and spacing of stabilizer guides, any suitable engagement structures, and any suitable closure mechanism in accordance with the principles of this disclosure.

Additional exemplary embodiments of the adjustable brace are discussed herein and made for a variety of injuries that may require immobilization in order for bones, muscles and/or tendons to heal. For example, the additional exemplary embodiments may include regions that may facilitate patient comfort (e.g., various upper extremity braces avoid the ulnar styloid process, radial styloid, and/or thumb MCP joint; various lower extremity braces include holes around the heel and/or around the malleolus; etc.). Additionally, a digital fabrication of the adjustable brace may be made based on a 3D scan of the patient and/or information gained from other medical imaging of the patient (e.g., X-rays). The positioning assumed by the patient during the 3D scan may be beneficial for comfort and healing. The patient-specific area of coverage may vary with particular medical use cases such that an adjustable brace may or may not immobilize an injured joint depending on the type of anatomy injured, the nature of the injury, patient comfort, and injury care considerations. For instance, if an injury involves the thumb, thumb joint immobilization may be needed; if an injury does not involve the thumb, an area may be left open around the thumb joint. Furthermore, additional holes may be included to the adjustable brace to facilitate rehabilitation with a bone stimulator (amongst other types of methods or devise) or to allow for improved injury care.

Figure 13:
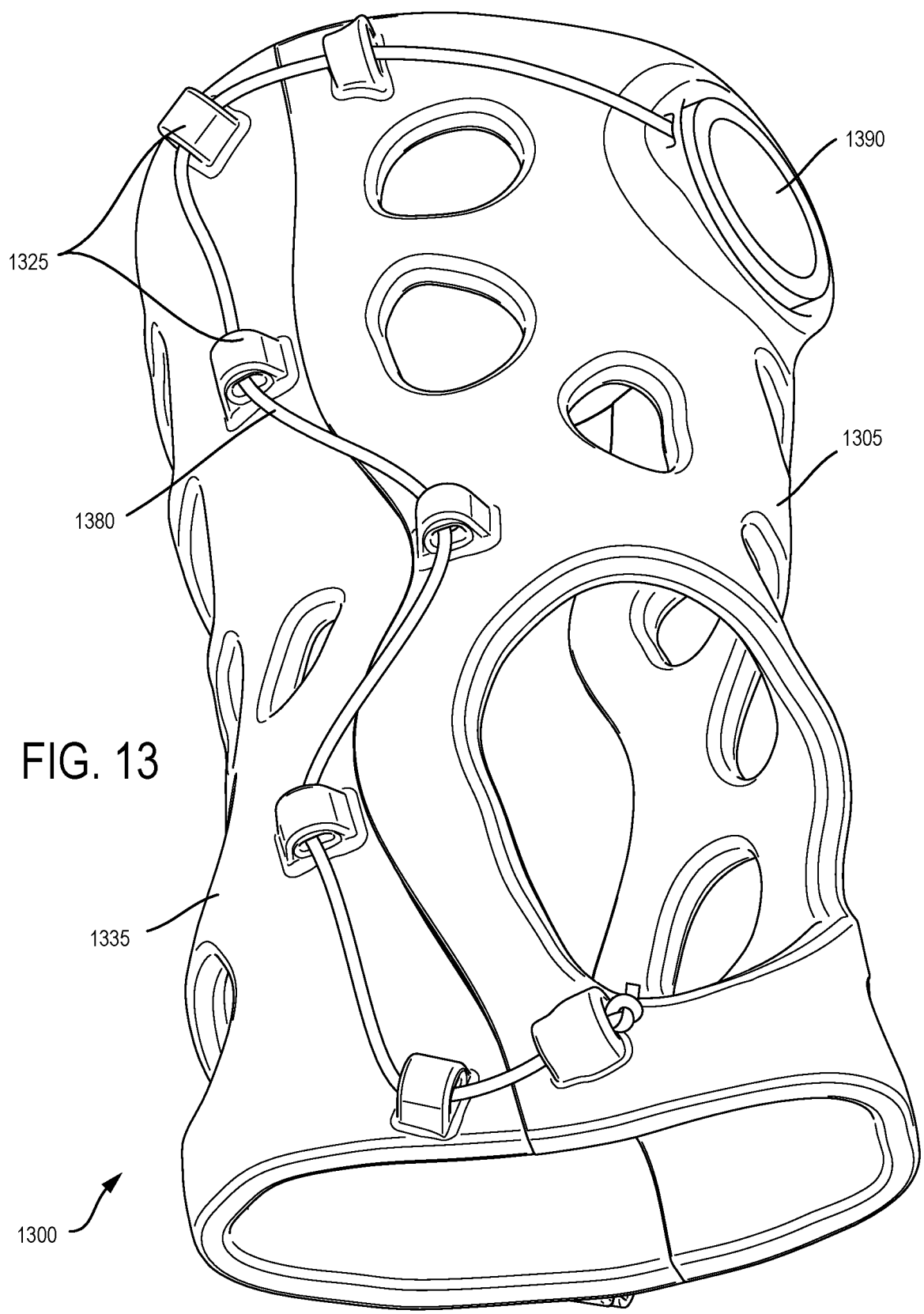
FIG. 13 is a perspective view of another embodiment of an assembled arm brace with closure mechanism in accordance with the principles of this disclosure.

FIG. 13 shows another exemplary fully assembled adjustable arm brace 1300. Similar to the adjustable brace of FIGS. 1-10, this embodiment includes a first stabilizer 1305 (conformal to the patient radius, wrist, and forearm) and second stabilizer 1335 (conformal to the patient ulna, wrist, and forearm), flexible lacing members 1380, and a closure mechanism 1390. Tabs disposed on the peripheries of the first stabilizer 1305 selectively engage with recesses disposed on the peripheries of the second stabilizer 1335. Flexible lacing members 1380 are threaded along stabilizer guides 1325 and around a closure mechanism 1390 in order to fully assemble the brace 1300. Adjustments to the closure mechanism 1390 selectively tighten or loosen the fit of the brace 1300 around a patient forearm.

Figure 14:
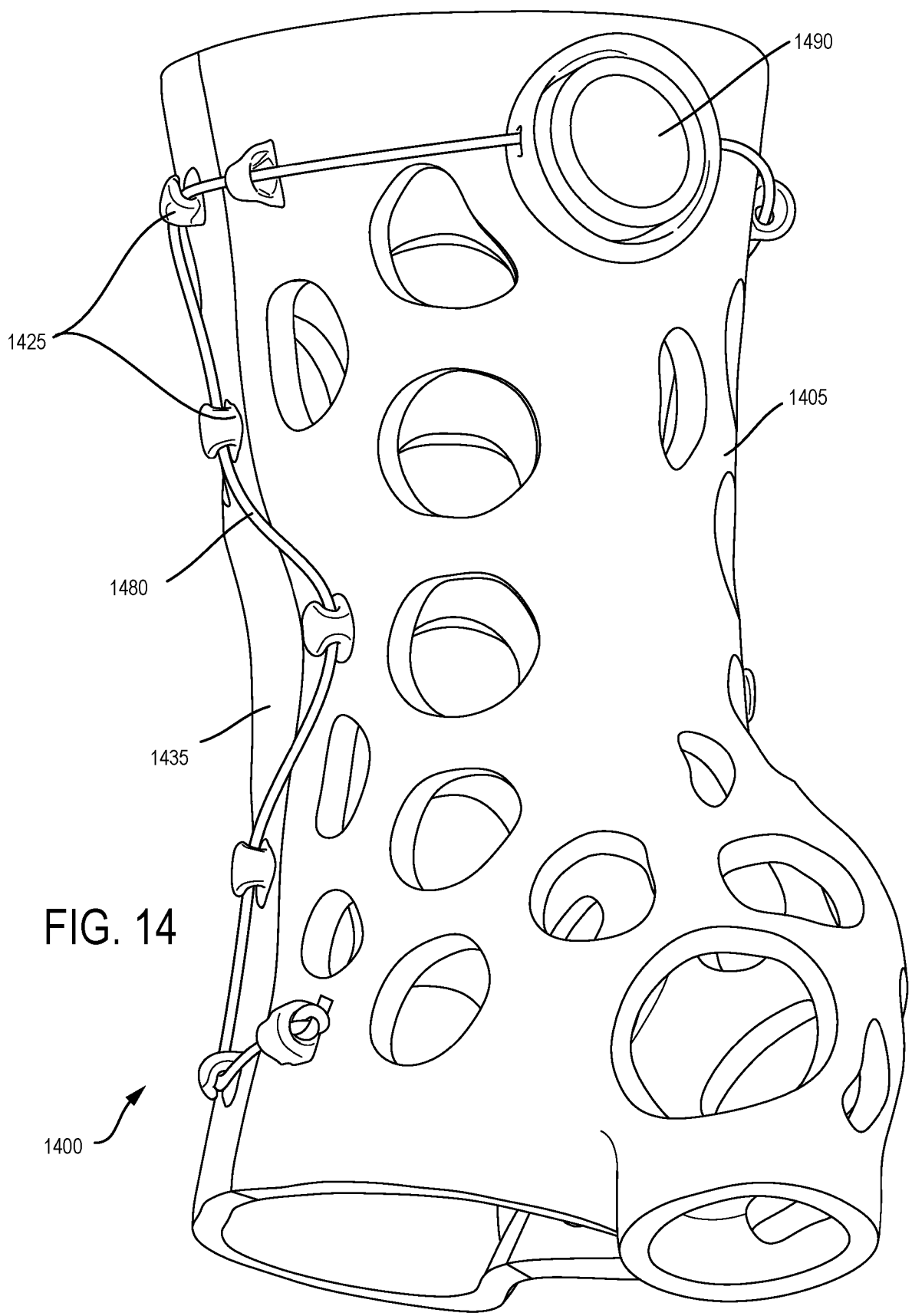
FIG. 14 is a perspective view of another embodiment of an assembled arm brace with closure mechanism in accordance with the principles of this disclosure.

FIG. 14 shows another exemplary fully assembled adjustable arm brace 1400. Similar to the adjustable brace of FIGS. 1-10, this embodiment includes a first stabilizer 1405 (conformal to the patient radius, wrist, and forearm) and second stabilizer 1435 (conformal to the patient ulna, wrist, and forearm), flexible lacing members 1480, and a closure mechanism 1490. Tabs disposed on the peripheries of the first stabilizer 1405 selectively engage with recesses disposed on the peripheries of the second stabilizer 1435. Flexible lacing members 1480 are threaded along stabilizer guides 1425 and around a closure mechanism 1490 in order to fully assemble the brace 1400. Adjustments to the closure mechanism 1490 selectively tighten or loosen the fit of the brace 1400 around a patient forearm.

Figure 15:
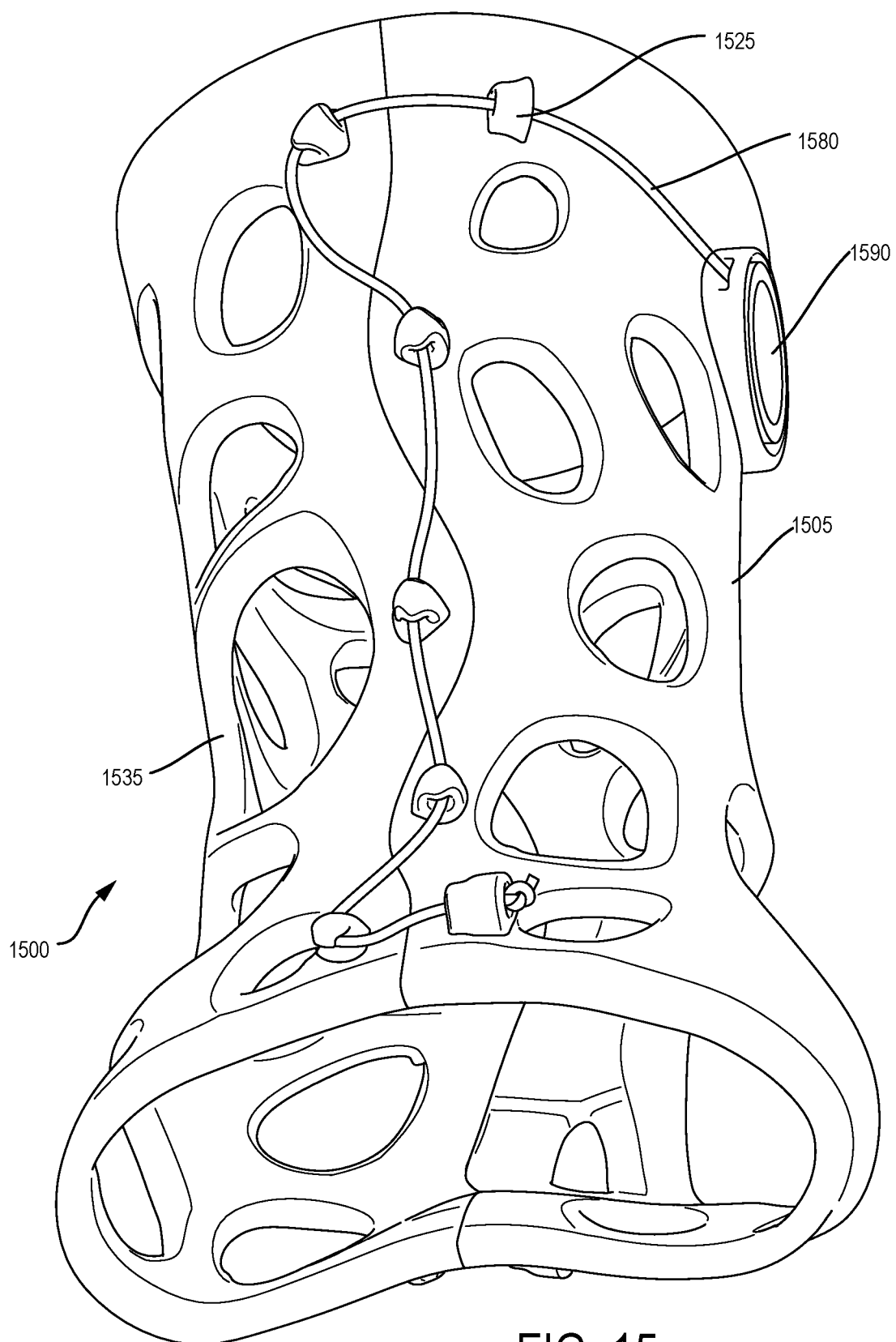
FIG. 15 is a perspective view of another embodiment of an assembled arm brace with closure mechanism in accordance with the principles of this disclosure.

FIG. 15 shows another exemplary fully assembled adjustable arm brace 1500. Similar to the adjustable brace of FIGS. 1-10, this embodiment includes a first stabilizer 1505 (conformal to the patient radius, wrist, and forearm) and second stabilizer 1535 (conformal to the patient ulna, wrist, and forearm), flexible lacing members 1580, and a closure mechanism 1590. Tabs disposed on the peripheries of the first stabilizer 1505 selectively engage with recesses disposed on the peripheries of the second stabilizer 1535. Flexible lacing members 1580 are threaded along stabilizer guides 1525 and around a closure mechanism 1590 in order to fully assemble the brace 1500. Adjustments to the closure mechanism 1590 selectively tighten or loosen the fit of the brace 1500 around a patient forearm.

Figure 16:
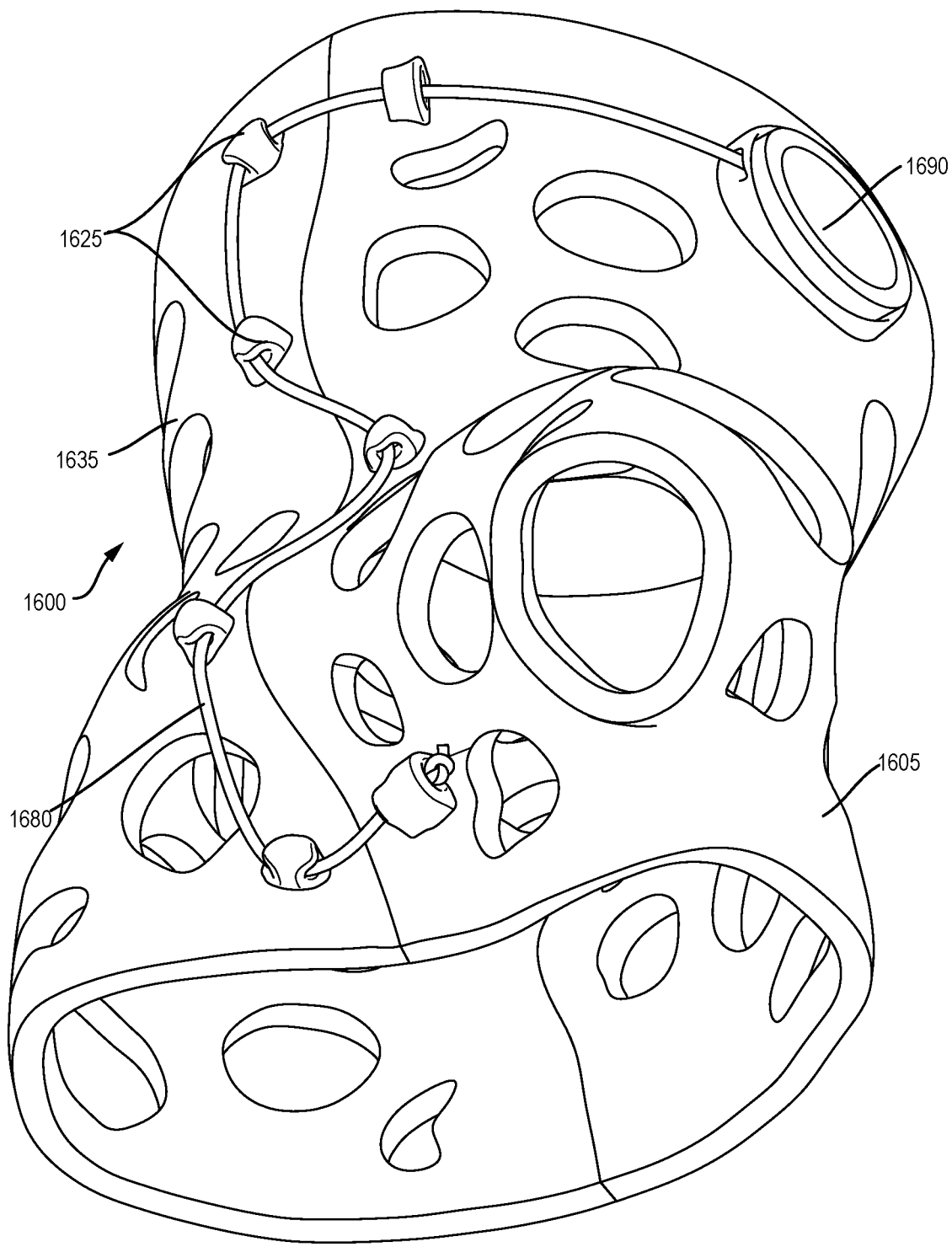
FIG. 16 is a perspective view of another embodiment of an assembled arm brace with closure mechanism in accordance with the principles of this disclosure.

FIG. 16 shows another exemplary fully assembled adjustable arm brace 1600. Similar to the adjustable brace of FIGS. 1-10, this embodiment includes a first stabilizer 1605 (conformal to the patient radius, wrist, and forearm) and second stabilizer 1635 (conformal to the patient ulna, wrist, and forearm), flexible lacing members 1680, and a closure mechanism 1690. Tabs disposed on the peripheries of the first stabilizer 1605 selectively engage with recesses disposed on the peripheries of the second stabilizer 1635. Flexible lacing members 1680 are threaded along stabilizer guides 1625 and around a closure mechanism 1690 in order to fully assemble the brace 1600. Adjustments to the closure mechanism 1690 selectively tighten or loosen the fit of the brace 1600 around a patient forearm.

Figure 17:
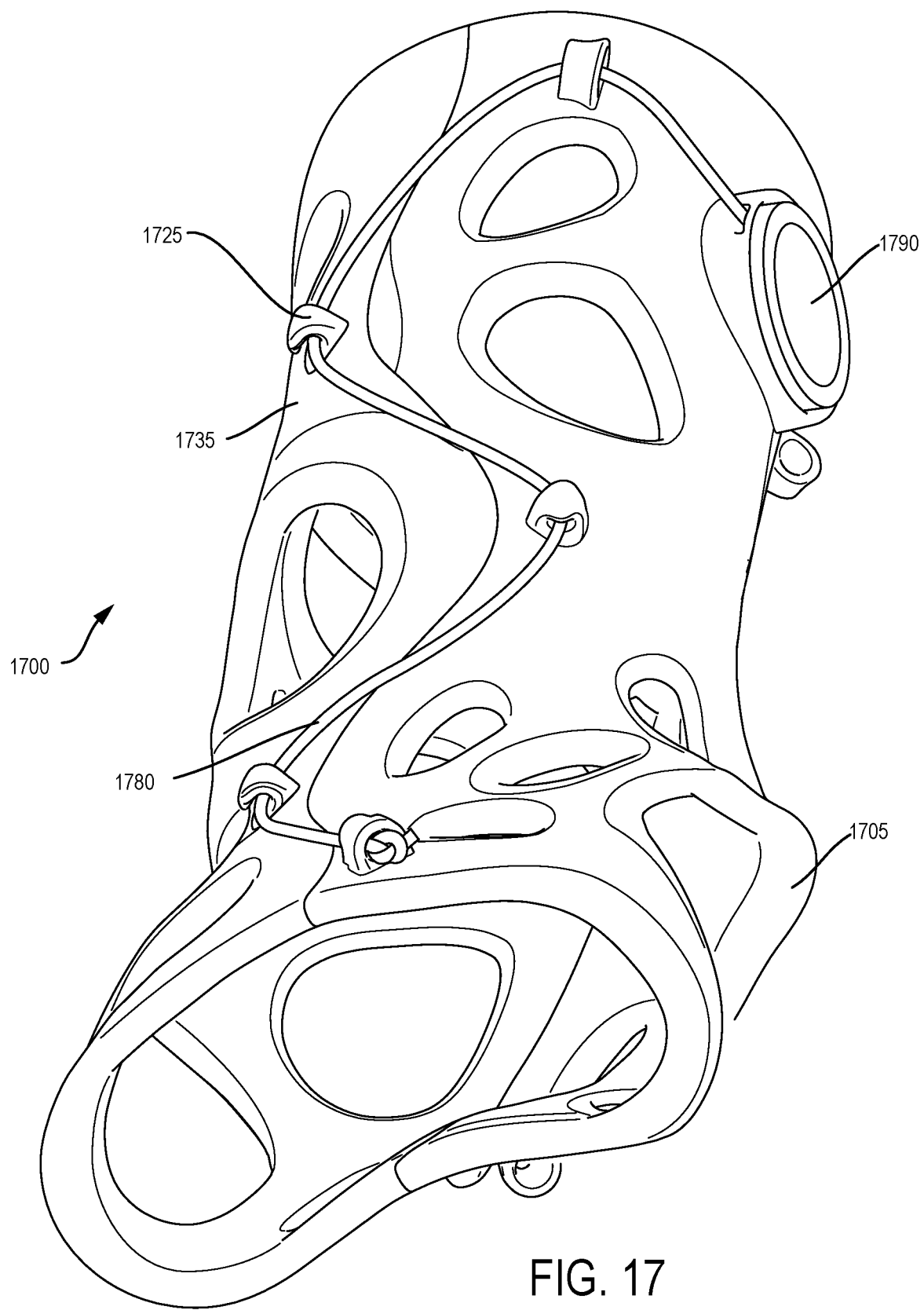
FIG. 17 is a perspective view of another embodiment of an assembled arm brace with closure mechanism in accordance with the principles of this disclosure.

FIG. 17 shows another exemplary fully assembled adjustable arm brace 1700. Similar to the adjustable brace of FIGS. 1-10, this embodiment includes a first stabilizer 1705 (conformal to the patient radius, wrist, and forearm) and second stabilizer 1735 (conformal to the patient ulna, wrist, and forearm), flexible lacing members 1780, and a closure mechanism 1790. Tabs disposed on the peripheries of the first stabilizer 1705 selectively engage with recesses disposed on the peripheries of the second stabilizer 1735. Flexible lacing members 1780 are threaded along stabilizer guides 1725 and around a closure mechanism 1790 in order to fully assemble the brace 1700. Adjustments to the closure mechanism 1790 selectively tighten or loosen the fit of the brace 1700 around a patient forearm.

Figure 18:
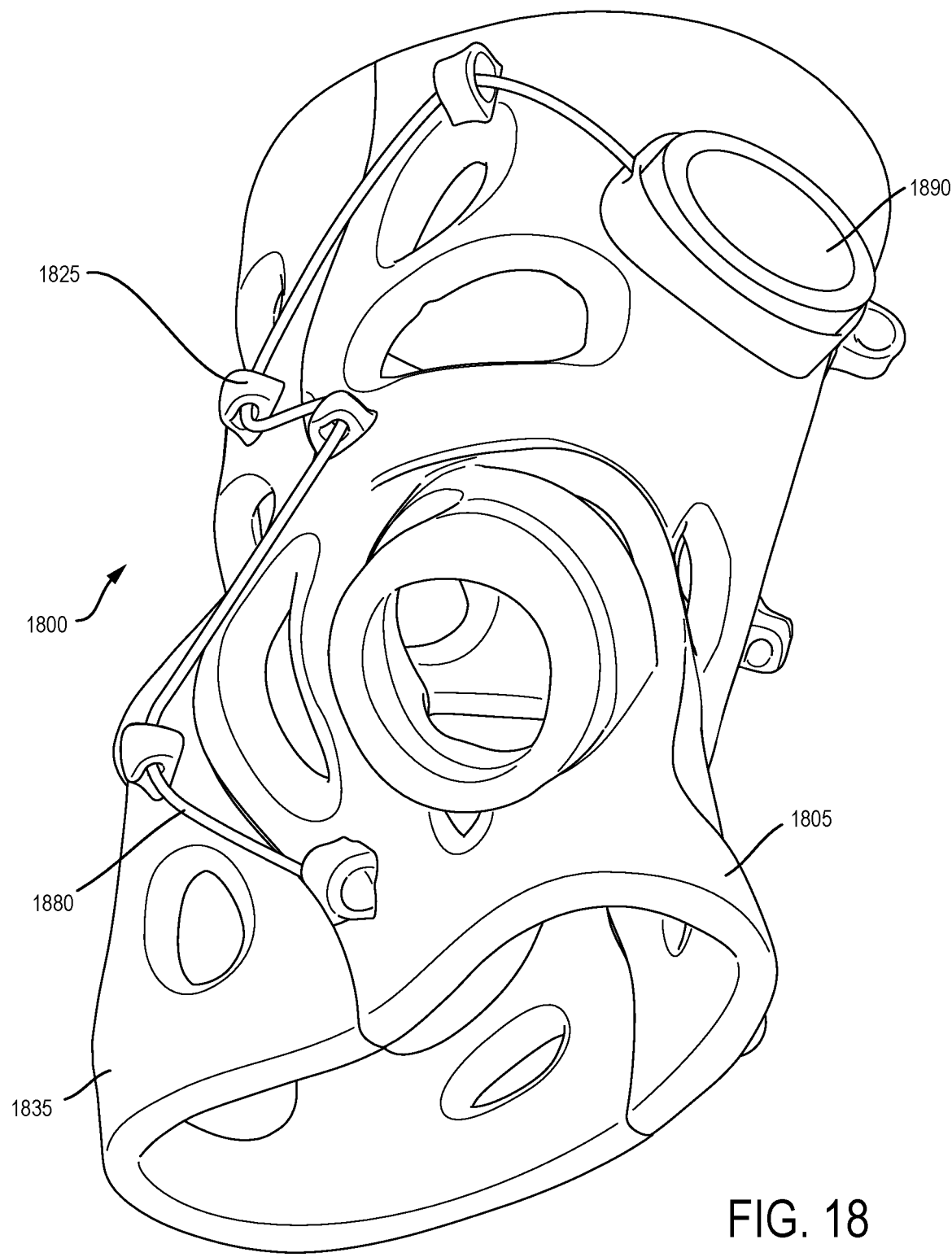
FIG. 18 is a perspective view of another embodiment of an assembled arm brace with closure mechanism in accordance with the principles of this disclosure.

FIG. 18 shows another exemplary fully assembled adjustable arm brace 1800. Similar to the adjustable brace of FIGS. 1-10, this embodiment includes a first stabilizer 1805 (conformal to the patient radius, wrist, and forearm) and second stabilizer 1835 (conformal to the patient ulna, wrist, and forearm), flexible lacing members 1880, and a closure mechanism 1890. Tabs disposed on the peripheries of the first stabilizer 1805 selectively engage with recesses disposed on the peripheries of the second stabilizer 1835. Flexible lacing members 1880 are threaded along stabilizer guides 1825 and around a closure mechanism 1890 in order to fully assemble the brace 1800. Adjustments to the closure mechanism 1890 selectively tighten or loosen the fit of the brace 1800 around a patient forearm.

Figure 19:
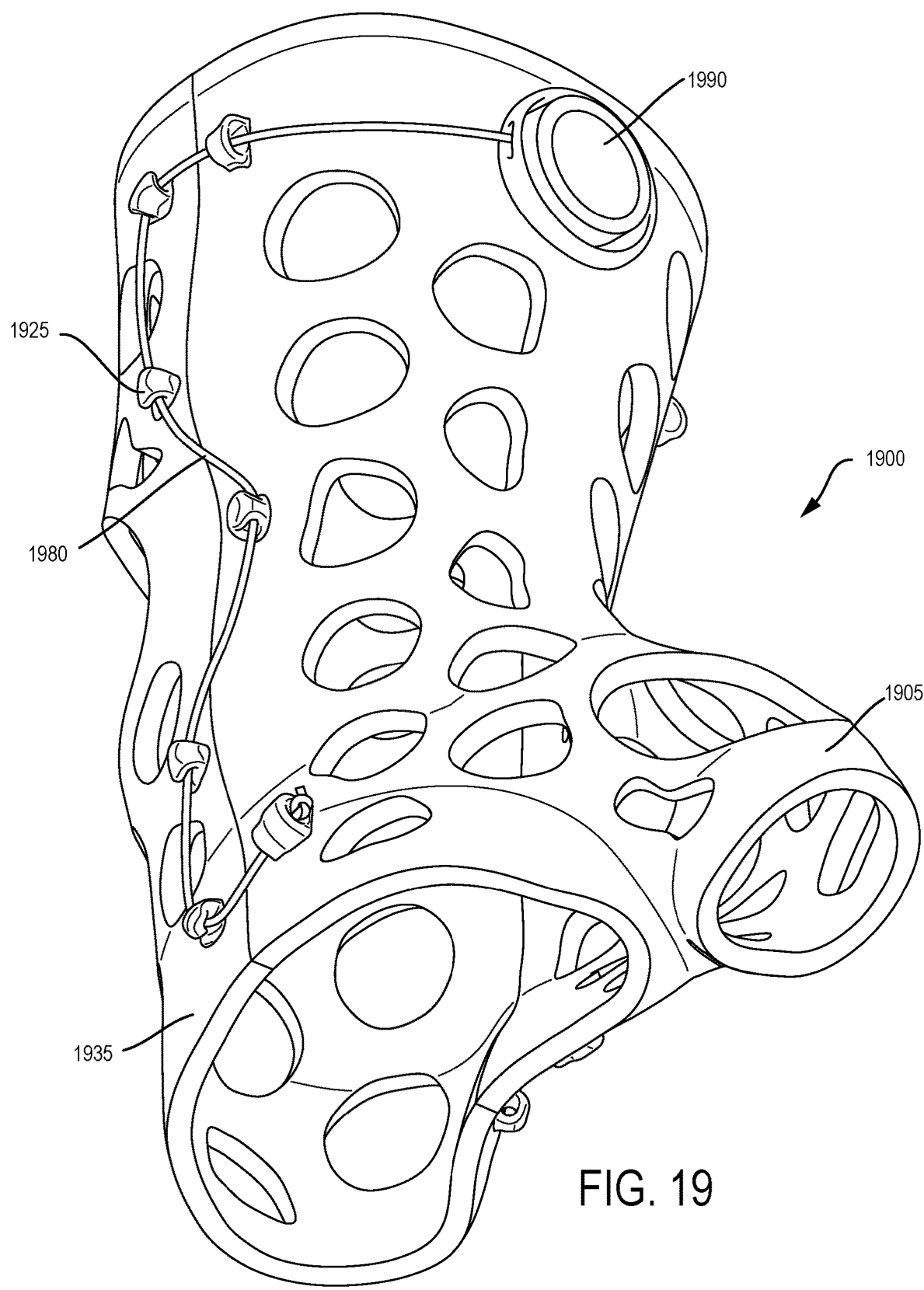
FIG. 19 is a perspective view of another embodiment of an assembled arm brace with closure mechanism in accordance with the principles of this disclosure.

FIG. 19 shows another exemplary fully assembled adjustable arm brace 1900. Similar to the adjustable brace of FIGS. 1-10, this embodiment includes a first stabilizer 1905 (conformal to the patient radius, wrist, and forearm) and second stabilizer 1935 (conformal to the patient ulna, wrist, and forearm), flexible lacing members 1980, and a closure mechanism 1990. Tabs disposed on the peripheries of the first stabilizer 1905 selectively engage with recesses disposed on the peripheries of the second stabilizer 1935. Flexible lacing members 1980 are threaded along stabilizer guides 1925 and around a closure mechanism 1990 in order to fully assemble the brace 1900. Adjustments to the closure mechanism 1990 selectively tighten or loosen the fit of the brace 1900 around a patient forearm.

FIG. 20 shows an exemplary fully assembled adjustable leg brace 2000. This embodiment includes a first stabilizer 2005 (for the anterior of a patient ankle), second stabilizer 2035 (for the anterior of a patient foot), third stabilizer 2055 (for the posterior of a full patient leg); flexible lacing members 2080; and a closure mechanism 2090. Tabs disposed on the peripheries of the stabilizers selectively engage with complementary recesses disposed on the peripheries of the stabilizers. Flexible lacing members 2080 are threaded through stabilizer guides 2025 and around a closure mechanism 2090 in order to fully assemble the brace 2000. Adjustments to the closure mechanism 2090 selectively tighten or loosen the fit of the brace 2000 around a patient leg.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

What is claimed is:

1. An adjustable brace for stabilizing a body part of a patient, the adjustable brace comprising:
   a first 3D printed stabilizer comprising a first exterior surface, a first interior surface, and a first thickness;
   a second 3D printed stabilizer comprising a second exterior surface, a second interior surface, and a second thickness;
   one or more attachment points;
   one or more selective engagement structures, the one or more selective engagement structures selected from the group consisting of one or more tabs and one or more recesses;

at least one flexible lacing member extending along a first stabilizer guide and a second stabilizer guide; and at least one closure mechanism coupled to the one or more attachment points, wherein:

the first 3D printed stabilizer selectively engages with the second 3D printed stabilizer at common peripheries of the first 3D printed stabilizer and second 3D printed stabilizer via the one or more selective engagement structures, respectively;

the flexible lacing member adjustably secures the first 3D printed stabilizer to the second 3D printed stabilizer;

a position of the first 3D printed stabilizer is adjustable in relation to the second 3D printed stabilizer at a particular distance based at least in part on a length of the one or more tabs;

the at least one closure mechanism comprises a spool and a control for selectively winding a length of the flexible lacing member around the spool to loosen or tighten the first 3D printed stabilizer and the second 3D printed stabilizer around the body part, thereby adjusting the position of the first 3D printed stabilizer in relation to the second 3D printed stabilizer the particular distance; and the spool comprises a periphery and a plurality of ratchet teeth disposed around the periphery, the ratchet teeth configured to selectively engage a pawl that inhibits rotation of the spool in one direction.

2. The adjustable brace of claim 1, wherein the flexible lacing member is removably attached to the spool such that the lacing member may be removed from the closure mechanism without removing the spool.

3. The adjustable brace of claim 2, wherein the first exterior surface forms the one or more attachment points.

4. The adjustable brace of claim 2, wherein the second exterior surface forms the one or more attachment points.

5. The adjustable brace of claim 1, wherein at least a portion of the first 3D printed stabilizer is made of resilient material.

6. The adjustable brace of claim 1, wherein at least a portion of the second 3D printed stabilizer is made of resilient material.

7. The adjustable brace of claim 1, wherein a first resilient cushion member extends from the first interior surface.

8. The adjustable brace of claim 1, wherein a second resilient cushion member extends from the second interior surface.

* * * * *